US011426231B2

(12) United States Patent
Germain et al.

(10) Patent No.: US 11,426,231 B2
(45) Date of Patent: Aug. 30, 2022

(54) ARTHROSCOPIC DEVICES AND METHODS

(71) Applicant: RELIGN Corporation, Cupertino, CA (US)

(72) Inventors: Aaron Germain, San Jose, CA (US); Ben Poser, Campbell, CA (US); Michael D. Walker, San Francisco, CA (US); Jan Echeverry, San Jose, CA (US)

(73) Assignee: Relign Corporation, Campbell, CA (US)

( * ) Notice: Subject to any disclaimer, the term of this patent is extended or adjusted under 35 U.S.C. 154(b) by 925 days.

(21) Appl. No.: 15/855,684

(22) Filed: Dec. 27, 2017

(65) Prior Publication Data
US 2019/0015151 A1    Jan. 17, 2019

Related U.S. Application Data

(60) Provisional application No. 62/445,117, filed on Jan. 11, 2017.

(51) Int. Cl.
*A61B 18/14* (2006.01)
*A61B 18/12* (2006.01)
(Continued)

(52) U.S. Cl.
CPC ...... *A61B 18/1482* (2013.01); *A61B 18/1206* (2013.01); *A61B 18/042* (2013.01);
(Continued)

(58) Field of Classification Search
CPC .... A61B 18/1482; A61B 18/14; A61B 18/042
See application file for complete search history.

(56) References Cited

U.S. PATENT DOCUMENTS 2,513,564 A    7/1950    Ingwersen
2,514,545 A    7/1950    Ingwersen
(Continued)

FOREIGN PATENT DOCUMENTS

DE    102005059864 A1    6/2007
EP         1034747 A1    9/2000
(Continued)

OTHER PUBLICATIONS

European search report dated Nov. 2, 2009 for EP Application No. 01967968.7.
(Continued)

*Primary Examiner* — Linda C Dvorak
*Assistant Examiner* — Annabeth E Rodriguez
(74) *Attorney, Agent, or Firm* — Schwegman Lundberg & Woessner, P.A.

(57) ABSTRACT

An arthroscopic or other medical device includes an elongate shaft having a proximal end and a working end. At least one electrode for treating tissue is located at the working end of the shaft, and a fluid outflow path extends proximally from the working end through a first channel portion in the shaft. A handpiece is coupled to the proximal end of the shaft and has a body with a second channel portion formed along an axis therein. The second channel is receives a heated or other outflow from a proximal end of the first channel in the shaft, and the second channel runs along an axis of the handpiece. A thin wall sleeve is located in the handpiece so that it surrounds at least a portion of the second channel. The thin wall sleeve is surrounded by an air gap or otherwise provides a thermal barrier between an exterior surface of the thin wall sleeve and an inner surface of the body of the handpiece in order to limit heat transfer from the heated or other fluid outflow through the second channel.

20 Claims, 24 Drawing Sheets

(51) Int. Cl.
*A61B 18/04* (2006.01)
*A61B 18/00* (2006.01)

(52) U.S. Cl.
CPC .............. *A61B 2018/00101* (2013.01); *A61B 2018/00577* (2013.01); *A61B 2018/00607* (2013.01); *A61B 2018/00619* (2013.01); *A61B 2018/00714* (2013.01); *A61B 2018/00791* (2013.01); *A61B 2218/007* (2013.01)

(56) References Cited

U.S. PATENT DOCUMENTS

| | | |
|---|---|---|
| 2,625,625 A | 1/1953 | Ingwersen |
| 2,689,895 A | 9/1954 | Ingwersen |
| 3,611,023 A | 10/1971 | Jesse, Jr. et al. |
| 3,838,242 A | 9/1974 | Goucher |
| 3,848,211 A | 11/1974 | Russell |
| 3,868,614 A | 2/1975 | Riendeau |
| 3,903,891 A | 9/1975 | Brayshaw |
| 4,060,088 A * | 11/1977 | Morrison, Jr ........ A61B 18/042 606/49 |
| 4,272,687 A | 6/1981 | Borkan |
| 4,781,175 A | 11/1988 | McGreevy et al. |
| 4,895,146 A | 1/1990 | Draenert |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,449,356 A | 9/1995 | Walbrink et al. |
| 5,490,854 A | 2/1996 | Fisher et al. |
| 5,602,449 A | 2/1997 | Krause et al. |
| 5,641,251 A | 6/1997 | Leins et al. |
| 5,669,907 A | 9/1997 | Platt, Jr. et al. |
| 5,683,366 A | 11/1997 | Eggers et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A * | 9/1998 | Rydell ............. A61B 17/32002 604/22 |
| 5,823,971 A | 10/1998 | Robinson et al. |
| 5,839,897 A | 11/1998 | Bordes |
| 5,849,010 A | 12/1998 | Wurzer et al. |
| 5,857,995 A | 1/1999 | Thomas et al. |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,964,752 A | 10/1999 | Stone |
| 5,989,248 A | 11/1999 | Tu et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,210,405 B1 | 4/2001 | Goble et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,245,084 B1 | 6/2001 | Mark et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,358,263 B2 | 3/2002 | Mark et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,419,684 B1 | 7/2002 | Heisler et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,610,059 B1 | 8/2003 | West et al. |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,837,884 B2 | 1/2005 | Woloszko |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,384,417 B2 * | 6/2008 | Cucin ............... A61B 17/32002 604/540 |
| 7,549,989 B2 | 6/2009 | Morgan et al. |
| 7,674,263 B2 | 3/2010 | Ryan |
| 7,678,069 B1 | 3/2010 | Baker et al. |
| 7,713,269 B2 | 5/2010 | Auge, II et al. |
| 7,717,710 B2 | 5/2010 | Danger et al. |
| 7,744,595 B2 | 6/2010 | Truckai et al. |
| 7,771,422 B2 | 8/2010 | Auge et al. |
| 7,819,861 B2 | 10/2010 | Auge et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |
| 8,221,404 B2 | 7/2012 | Truckai |
| 8,323,280 B2 | 12/2012 | Germain et al. |
| 8,333,763 B2 | 12/2012 | Truckai et al. |
| 8,372,068 B2 | 2/2013 | Truckai |
| 8,486,096 B2 | 7/2013 | Robertson et al. |
| 8,702,702 B1 | 4/2014 | Edwards et al. |
| 9,179,923 B2 | 11/2015 | Gubellini et al. |
| 9,204,918 B2 | 12/2015 | Germain et al. |
| 9,277,954 B2 | 3/2016 | Germain et al. |
| 9,504,521 B2 | 11/2016 | Deutmeyer et al. |
| 9,585,675 B1 | 3/2017 | Germain et al. |
| 9,592,085 B2 | 3/2017 | Germain et al. |
| 9,603,656 B1 | 3/2017 | Germain et al. |
| 9,681,913 B2 | 6/2017 | Orczy-Timko et al. |
| 9,795,434 B2 | 10/2017 | Germain et al. |
| 10,022,140 B2 | 7/2018 | Germain et al. |
| 10,327,842 B2 | 6/2019 | Germain et al. |
| 10,568,685 B2 | 2/2020 | Germain et al. |
| 10,582,966 B2 | 3/2020 | Orczy-Timko et al. |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0024396 A1 * | 2/2004 | Eggers ............... A61B 18/1482 606/39 |
| 2004/0044341 A1 | 3/2004 | Truckai et al. |
| 2004/0073195 A1 * | 4/2004 | Cucin ............. A61B 17/32002 604/542 |
| 2004/0167427 A1 | 8/2004 | Quick et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0074345 A1 | 4/2006 | Hibner |
| 2006/0178670 A1 | 8/2006 | Woloszko et al. |
| 2006/0200123 A1 * | 9/2006 | Ryan ................... A61B 18/148 606/48 |
| 2006/0224154 A1 | 10/2006 | Shadduck et al. |
| 2007/0213704 A1 | 9/2007 | Truckai et al. |

(56) References Cited

U.S. PATENT DOCUMENTS

| | | |
|---|---|---|
| 2008/0003255 A1 | 1/2008 | Kerr et al. |
| 2008/0103494 A1 | 5/2008 | Rioux et al. |
| 2008/0188848 A1 | 8/2008 | Deutmeyer et al. |
| 2008/0208249 A1 | 8/2008 | Blain et al. |
| 2009/0048485 A1 | 2/2009 | Heisler |
| 2009/0076498 A1 | 3/2009 | Saadat et al. |
| 2009/0270849 A1 | 10/2009 | Truckai et al. |
| 2010/0100091 A1 | 4/2010 | Truckai |
| 2010/0305565 A1 | 12/2010 | Truckai et al. |
| 2011/0282373 A1 | 11/2011 | Chekan et al. |
| 2012/0209112 A2 | 8/2012 | Patel et al. |
| 2012/0245580 A1 | 9/2012 | Germain et al. |
| 2012/0330292 A1* | 12/2012 | Shadduck .............. A61B 18/18  606/13 |
| 2013/0122461 A1 | 5/2013 | Shioiri |
| 2013/0172870 A1 | 7/2013 | Germain et al. |
| 2013/0267937 A1 | 10/2013 | Shadduck et al. |
| 2013/0296847 A1 | 11/2013 | Germain et al. |
| 2013/0296849 A1 | 11/2013 | Germain et al. |
| 2013/0317493 A1 | 11/2013 | Truckai et al. |
| 2013/0331833 A1 | 12/2013 | Bloom |
| 2014/0100567 A1 | 4/2014 | Edwards et al. |
| 2014/0135806 A1 | 5/2014 | Shener-Irmakoglu et al. |
| 2014/0336643 A1 | 11/2014 | Orczy-Timko et al. |
| 2015/0245862 A1 | 9/2015 | Goode et al. |
| 2015/0265337 A1 | 9/2015 | Bloom |
| 2017/0128083 A1 | 5/2017 | Germain et al. |
| 2017/0172648 A1 | 6/2017 | Germain et al. |
| 2017/0224368 A1 | 8/2017 | Germain et al. |
| 2017/0252099 A1 | 9/2017 | Orczy-Timko et al. |
| 2018/0263649 A1 | 9/2018 | Germain et al. |
| 2018/0303509 A1 | 10/2018 | Germain et al. |
| 2020/0060752 A1 | 2/2020 | Germain et al. |
| 2020/0163710 A1 | 5/2020 | Germain et al. |

FOREIGN PATENT DOCUMENTS

| | | |
|---|---|---|
| JP | 2002509756 A | 4/2002 |
| JP | 2015180290 A | 10/2015 |
| WO | WO-9949799 A1 | 10/1999 |
| WO | WO-0053112 A2 | 9/2000 |
| WO | WO-0062685 A1 | 10/2000 |
| WO | WO-0053112 A3 | 12/2000 |
| WO | WO-0124720 A1 | 4/2001 |
| WO | WO-2007073867 A1 | 7/2007 |
| WO | WO-2013052250 A1 | 4/2013 |
| WO | WO-2016171963 A1 | 10/2016 |
| WO | WO-2017070486 A1 | 4/2017 |
| WO | WO-2017070510 A1 | 4/2017 |
| WO | WO-2017136414 A1 | 8/2017 |

OTHER PUBLICATIONS

International search report and opinion dated Jul. 15, 2016 for PCT/US2016/027157.
International Search Report and Written Opinion dated Mar. 8, 2017 for International PCT Patent Application No. PCT/US2016/058179.
International Search Report and Written Opinion dated May 16, 2017 for International PCT Patent Application No. PCT/US2017/016002.
International Search Report and Written Opinion dated May 23, 2012 for International PCT Patent Application No. PCT/US2012/023390.
International Search Report and Written Opinion dated Nov. 29, 2016 for International Application No. PCT/US2016/058145.
International search report dated Jan. 14, 2002 for PCT/US2001/025409.
Kim, et al. Optical feedback signal for ultra short pulse ablation of tissue. Appl. Surface Sci. 1998; 127-129:857-862.
Notice of Allowance dated Jan. 6, 2017 for U.S. Appl. No. 14/960,084.
Notice of Allowance dated Feb. 8, 2017 for U.S. Appl. No. 14/977,256.
Notice of Allowance dated Feb. 16, 2017 for U.S. Appl. No. 15/096,546.
Notice of allowance dated Mar. 19, 2018 for U.S. Appl. No. 15/421,264.
Notice of Allowance dated Dec. 2, 2016 for U.S. Appl. No. 14/977,256.
Notice of Allowance dated Dec. 30, 2016 for U.S. Appl. No. 14/977,256.
Office action dated May 3, 2016 for U.S. Appl. No. 14/960,084.
Office Action dated Jul. 21, 2017 for U.S. Appl. No. 15/421,264.
Office action dated Jul. 28, 2016 for U.S. Appl. No. 14/977,256.
Office Action dated Aug. 18, 2016 for U.S. Appl. No. 14/960,084.
Office Action dated Sep. 26, 2016 for U.S. Appl. No. 15/096,546.
Office action dated Nov. 3, 2017 for U.S. Appl. No. 15/449,796.
Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.
Tucker et al. Histologic characteristics of electrosurgical injuries. J. Am. Assoc. Gyneco. Laproscopy. 1997; 4(2):857-862.
Volpato, et al., Application of Zirconia in Dentistry: Biological, Mechanical and Optical Considerations. Advances in ceramics— electric and magnetic ceramics, bioceramics, ceramics and environment. Sep. 2011.
Co-pending U.S. Appl. No. 16/780,041, inventors Orczy-Timko; Benedek et al., filed Feb. 3, 2020.
European search report and opinion dated May 15, 2019 for EP Application No. 16858321.9.
European search report and opinion dated Jul. 12, 2019 for EP Application No. 17748056.3.
Notice of Allowance dated Feb. 4, 2019 for U.S. Appl. No. 15/449,796.
Notice of Allowance dated Mar. 7, 2019 for U.S. Appl. No. 15/449,796.
Notice of Allowance dated Oct. 17, 2019 for U.S. Appl. No. 15/415,721.
Notice of Allowance dated Nov. 1, 2019 for U.S. Appl. No. 15/599,372.
Office action dated Apr. 27, 2020 for U.S. Appl. No. 15/920,130.
Office action dated May 8, 2019 for U.S. Appl. No. 15/415,721.
Office action dated Jul. 6, 2018 for U.S. Appl. No. 15/449,796.
Office action dated Dec. 12, 2018 for U.S. Appl. No. 15/415,721.

\* cited by examiner

ARTHROSCOPIC DEVICES AND METHODS

CROSS-REFERENCE TO RELATED APPLICATION

This application claims the benefit of provisional application 62/445,117, filed on Jan. 11, 2017, the full disclosure of which is incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing soft tissue with an electrosurgical device.

In several surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

Many such procedures are performed in a fluid and/or saline-filled field where the fluid becomes heated and is removed through an aspiration lumen or passage which passes through a shaft and a handpiece of the tools. In such cases, heating of the handpiece can be problematic, particularly when the handpiece also caries motors and electronics for performing the procedure.

For these reasons, a need exists for arthroscopic shavers, cutters, and other laparoscopic and surgical tools that in addition to cutting and removing bone and soft tissue, provide for improved and reliable thermal management within the tool handpiece or similar structure. At least some of these objectives will be met by the inventions described herein below.

2. Description of the Background Art

Commonly owned related patents include U.S. Pat. Nos. 8,323,280; 9,204,918; 9,277,954; 9,585,675; 9,592,085; 9,603,656; 9,795,434.

SUMMARY OF THE INVENTION

In a first aspect, the present invention provides an arthroscopic or other medical device comprising an elongate shaft having a proximal end and a working end. At least one electrode for treating tissue is located at the working end of the shaft, and a fluid outflow path extends proximally from the working end through a first channel portion in the shaft. A handpiece coupled to the proximal end of the shaft comprises a body with a second channel portion formed along an axis therein. The second channel is configured to receive a heated or other outflow from a proximal end of the first channel in the shaft, and the second channel runs along an axis of the handpiece. A thin wall sleeve is located in the handpiece so that it surrounds at least a portion of the second channel. The thin wall sleeve is surrounded by an air gap between an exterior surface of the thin wall sleeve and an inner surface of the body in order to limit heat transfer from the heated or other fluid outflow through the second channel.

In specific examples, the thin wall sleeve may comprise a material having a thermal conductivity of less than 50 W/m·K., often having a thermal conductivity of less than 25 W/m·K. A fluid-tight chamber may be disposed in the handpiece to provide or define the air gap. The air gap may have a width transverse to the axis of at least 0.005" and the thin wall sleeve may extend over at least 60% of a length of the second channel portion in the handpiece, frequently extending over at least 80% of a length of the second channel portion in the handpiece, and often extending over substantially the entire length of the second channel portion in the handpiece. Often, the shaft includes a proximal hub and so that it is detachable from the handpiece, allowing the handpiece to be cleaned and re-used while the shaft component is disposable. The handpiece may carry a motor and other system drive and control components for moving a component of the working end.

In a second aspect, the present invention provides an arthroscopic or other medical device comprising a handpiece having a body. A shaft having a proximal end attachable to a distal end of the handpiece extends distally from to a working end, and at least one electrode for treating tissue is located at the working end of the shaft. A fluid flow path extends from the working end proximally through a lumen in the shaft and through a channel in the handpiece. A sleeve is disposed in the lumen in the handpiece, where the sleeve and a surrounding portion of the body have a combined thermal conductivity in a transverse direction of less than 50 W/m·K, often less than 25 W/m·K, for limiting heat transfer from a fluid flow through the channel to the handpiece.

In specific examples, the sleeve may be formed at least partly of a material selected from a group consisting of metal, ceramic or glass, for example being formed at least partly of stainless steel, being formed at least partly of a metal with a ceramic surface layer, or being formed at least partly of a ceramic which comprises an exterior or interior surface of the sleeve. The sleeve may be substantially surrounded by an air gap disposed between an exterior surface of the sleeve and an interior surface of the handpiece body, where the air gap may be formed or defined by a fluid-tight chamber in the handpiece. The air gap may have a width transverse to the axis of at least 0.005" and the thin wall sleeve may extend over at least 60% of a length of the second channel portion in the handpiece, frequently extending over at least 80% of a length of the second channel portion in the handpiece, and often extending over substantially the entire length of the second channel portion in the handpiece.

In a third aspect, the present invention provides a method of treating a patient's tissue comprising providing a handpiece coupled to an elongate shaft having an electrosurgical working end. The electrosurgical working end is introduced into a fluid-immersed tissue treatment site in the patient's body, and the electrosurgical working end is energized or otherwise activated to treat tissue which typically causes fluid in the site to become heated. A negative pressure source coupled to the handpiece is activated to initiate an outflow of heated fluid through a flow path through the shaft and the handpiece. Heat transfer from the flow of heated fluid through the handpiece is limited to maintain the handpiece temperature at temperature suitable for gripping with a human hand.

In specific examples of these methods, the limiting step may comprise surrounding the flow path through the handpiece in a sleeve with an air gap. Alternatively or additionally, the limiting step may comprise surrounding the flow path through the handpiece in a sleeve with a material having a thermal conductivity of less than 50 W/m·K, often being less than 25 W/m·K. The sleeve may be formed at least partly of a material selected from a group consisting of metal, ceramic or glass, for example being formed at least partly of stainless steel, being formed at least partly of a metal with a ceramic surface layer, being formed at least partly of a ceramic which comprises an exterior or interior surface of the sleeve or the ceramic may comprise a surface of the lumen of the sleeve.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

FIG. 23 is a sectional view of another variation of a handpiece that includes a fluid outflow channel with a surrounding air gap to prevent unwanted heating of the handpiece body.

DETAILED DESCRIPTION OF THE INVENTION

The present invention relates to bone cutting and removal devices and related methods of use. Several variations of the invention will now be described to provide an overall understanding of the principles of the form, function and methods of use of the devices disclosed herein. In general, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 rpm to 20,000 rpm.

Figure 1:
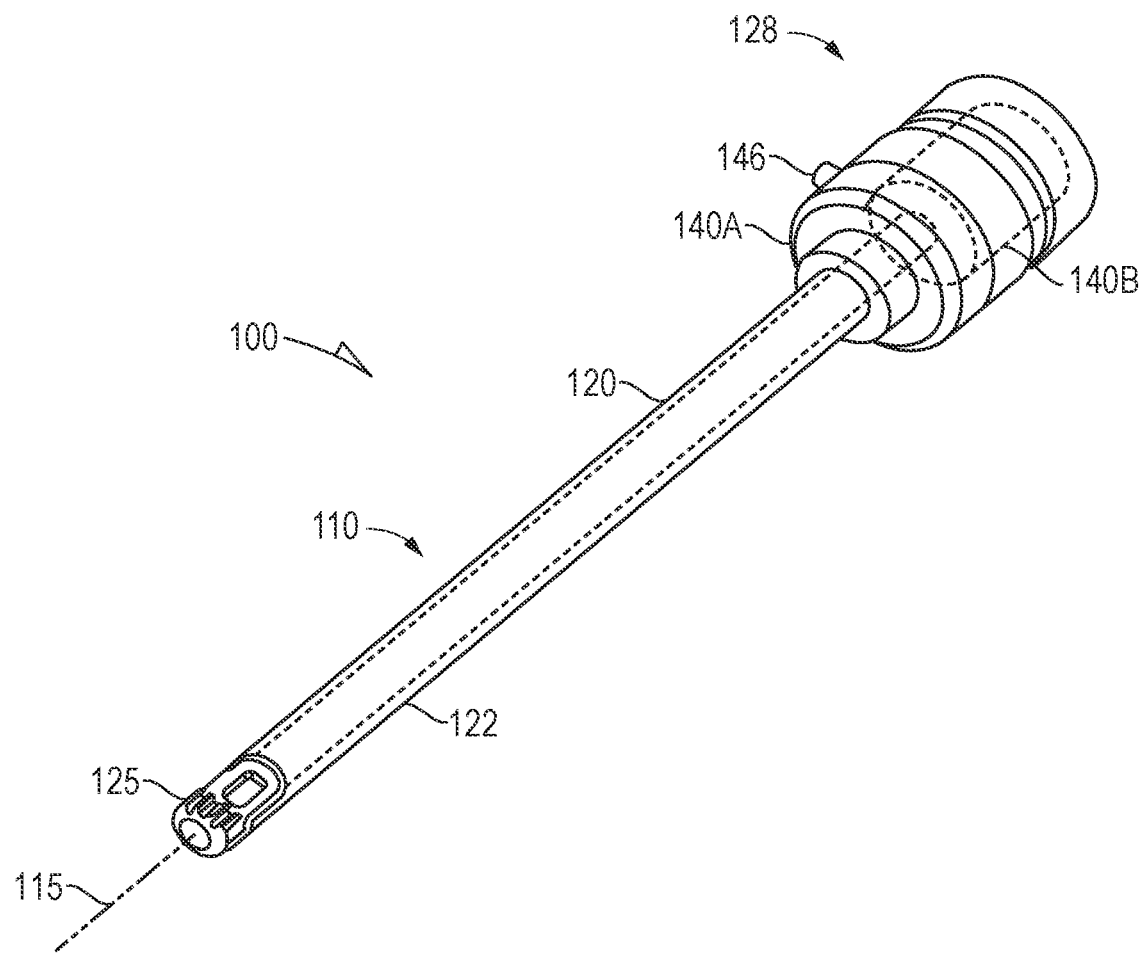
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
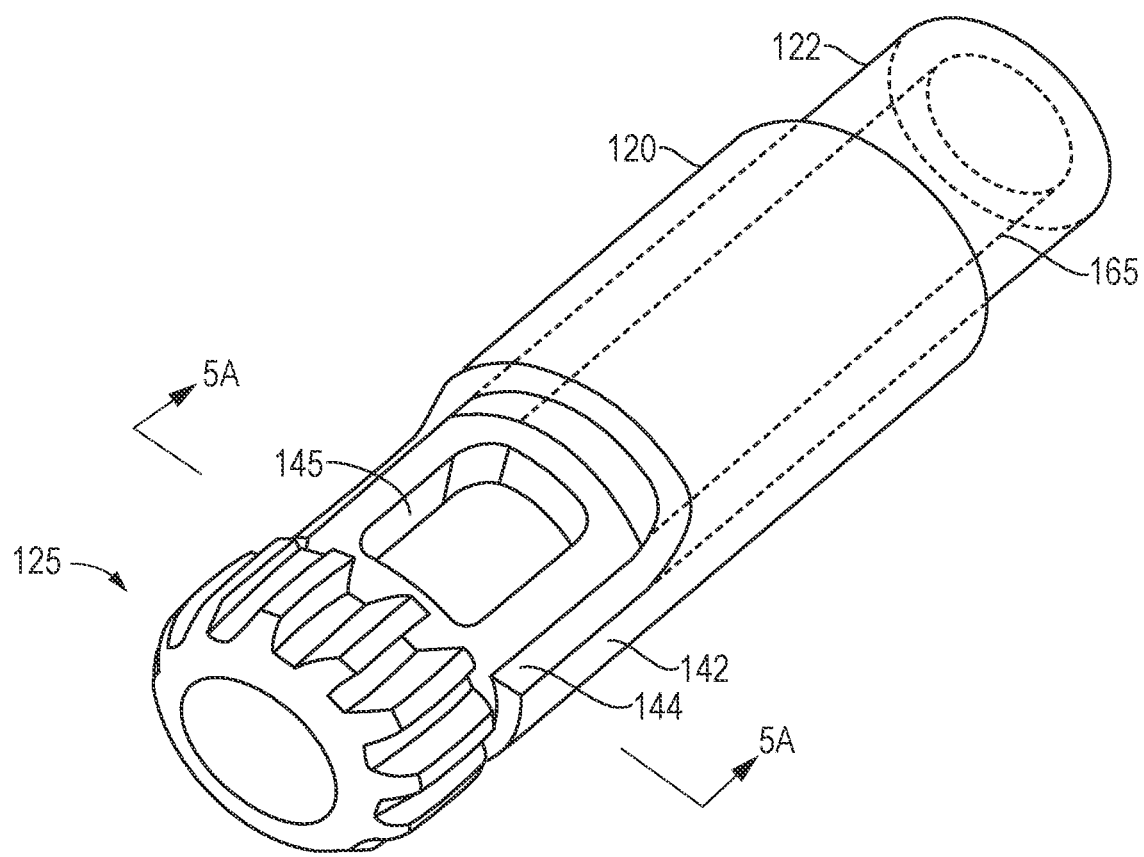
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in a manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 ands 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104. As can be seen in FIG. 1, the outer hub 140A includes a projecting key 146 that is adapted to mate with a receiving J-lock slot 148 in the handle 104 (see FIG. 3).

Figure 3:
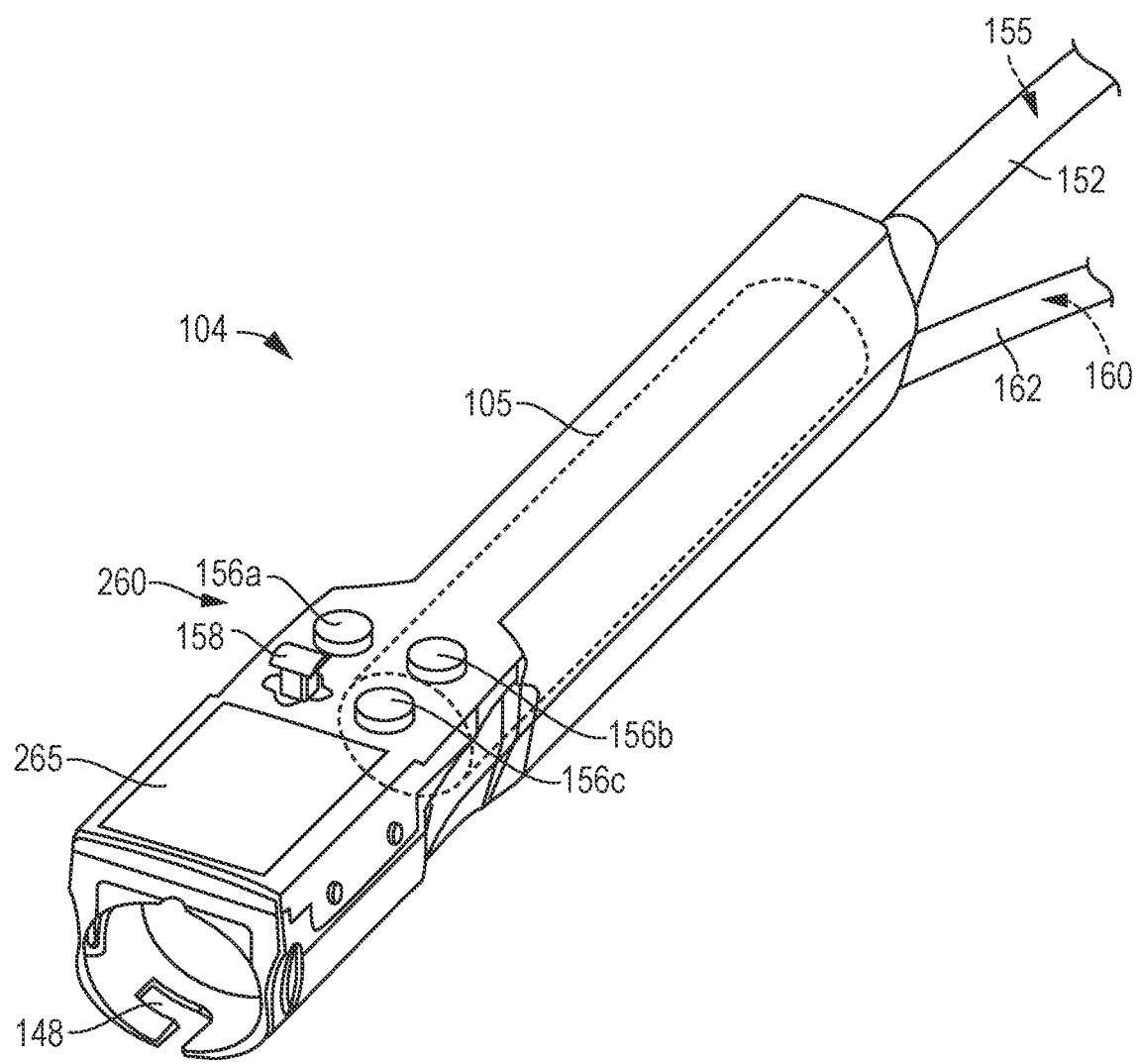
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 rpm. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
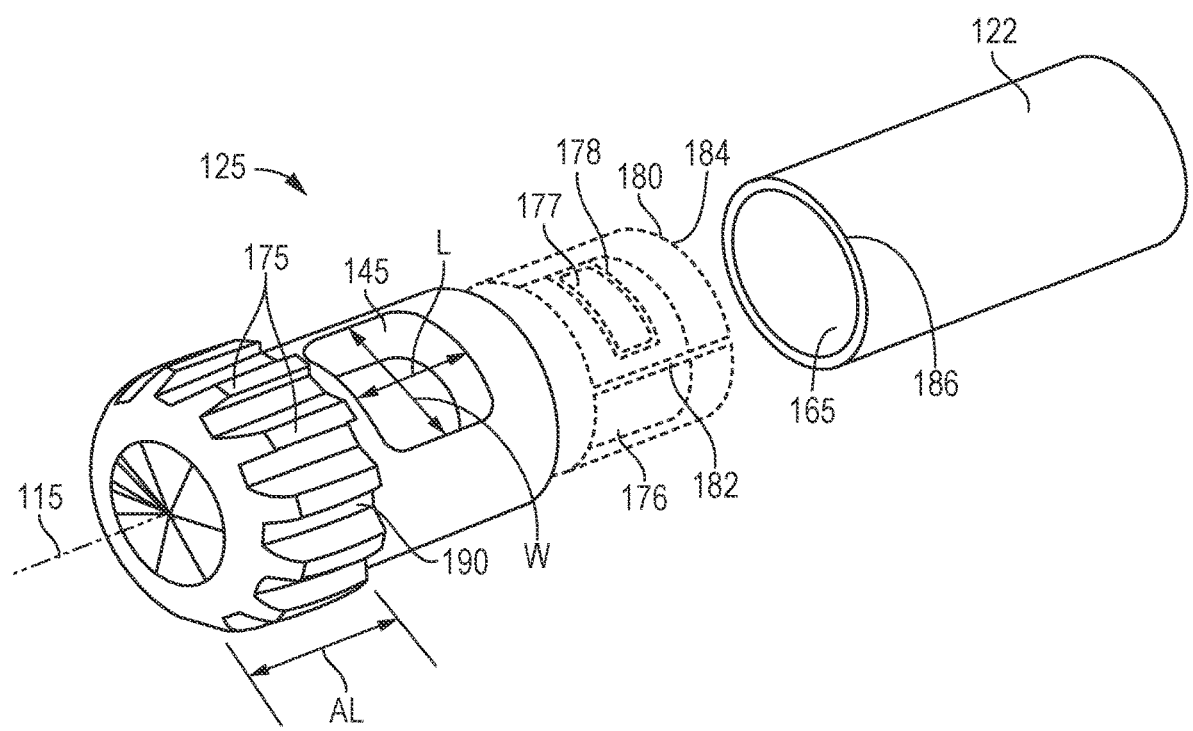
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

| | Hardness (GPa) | Fracture Toughness ($MPam^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) | | | |
| Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) | | | |
| YTA-14 (Superior Technical Ceramics) | 14.0 | 5 | 2.80:1 |
| ZTA (CoorsTek) | 14.8 | 6 | 2.47:1 |
| Ceria stabilized zirconia | | | |
| CSZ (Superior Technical Ceramics) | 11.7 | 12 | 0.98:1 |
| Silicon Nitride | | | |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics—Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 Gpa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 ($1 \times 10^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
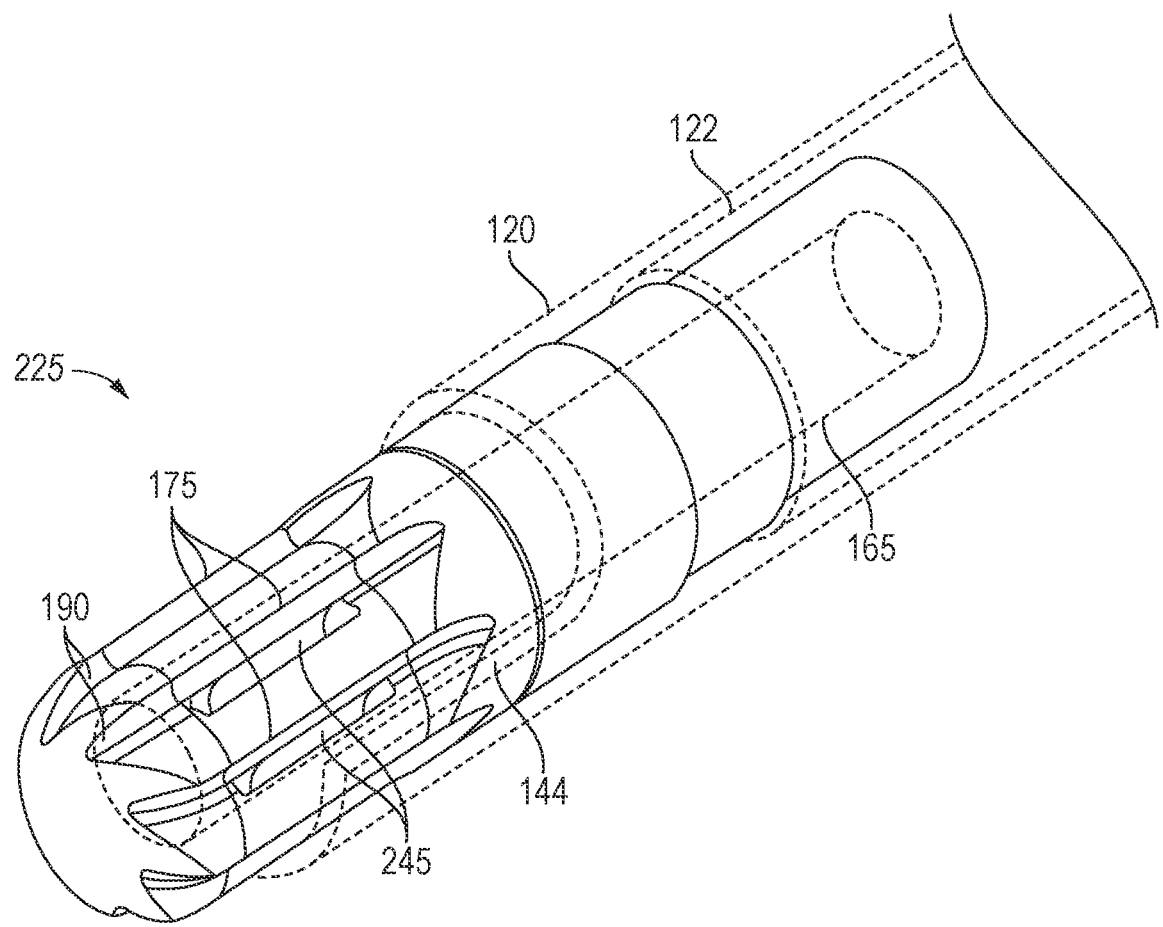
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
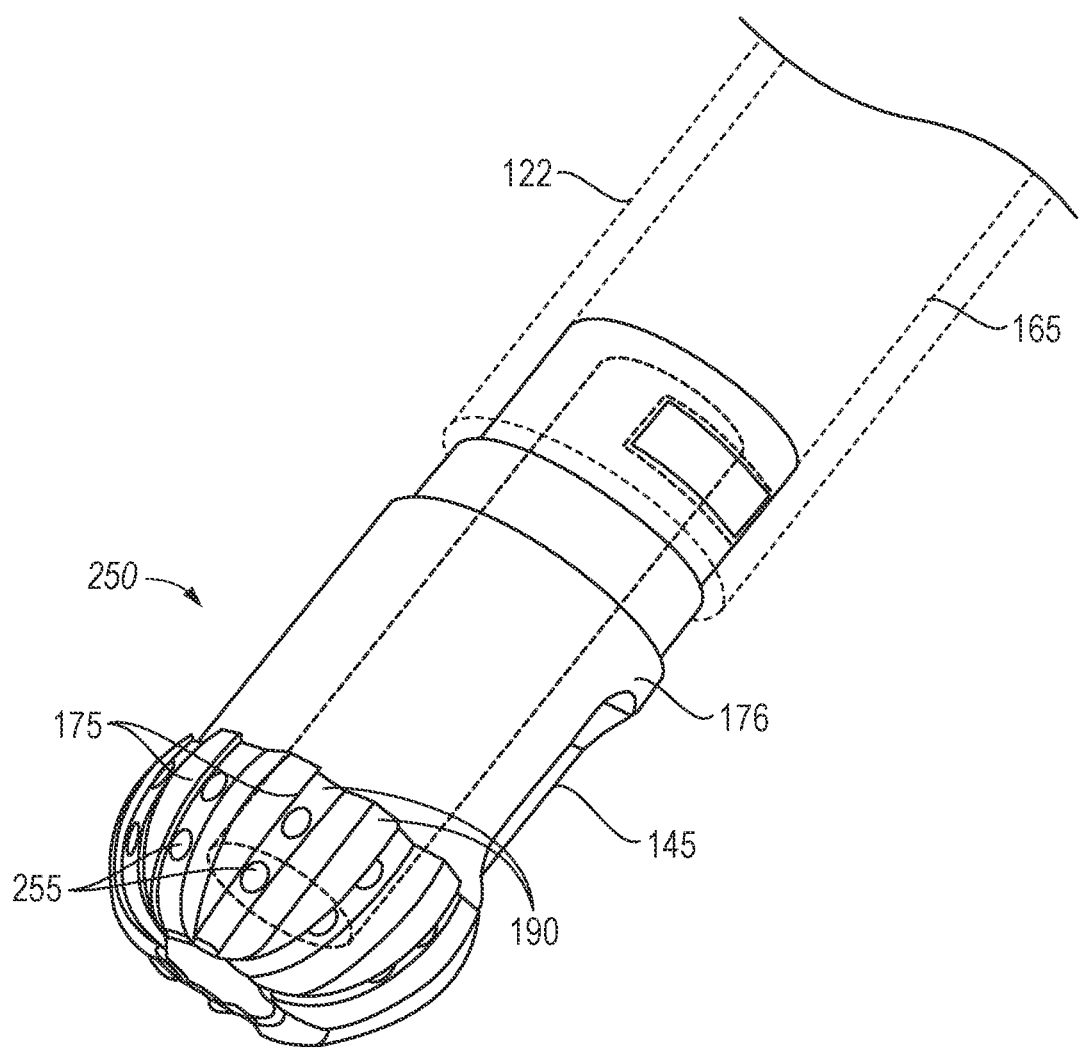
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
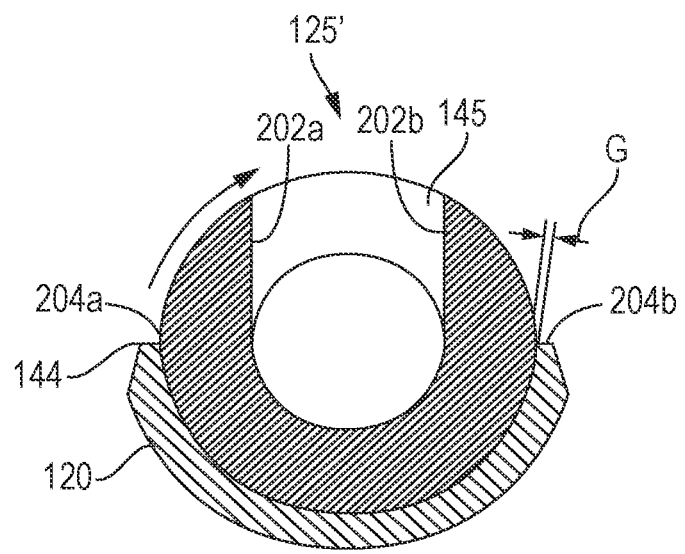
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
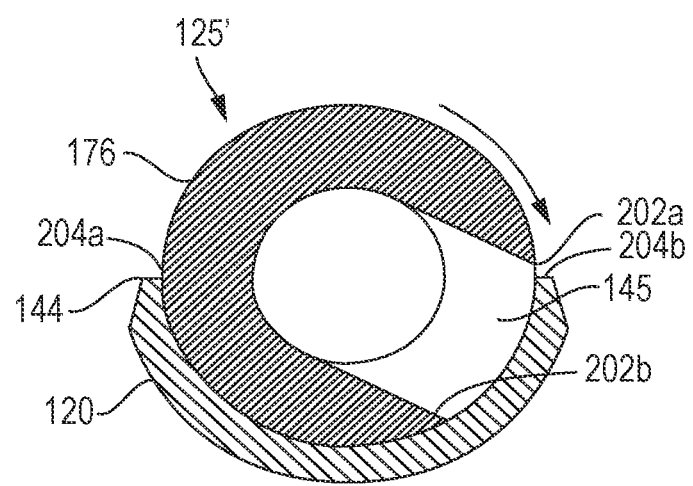
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 Gpa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
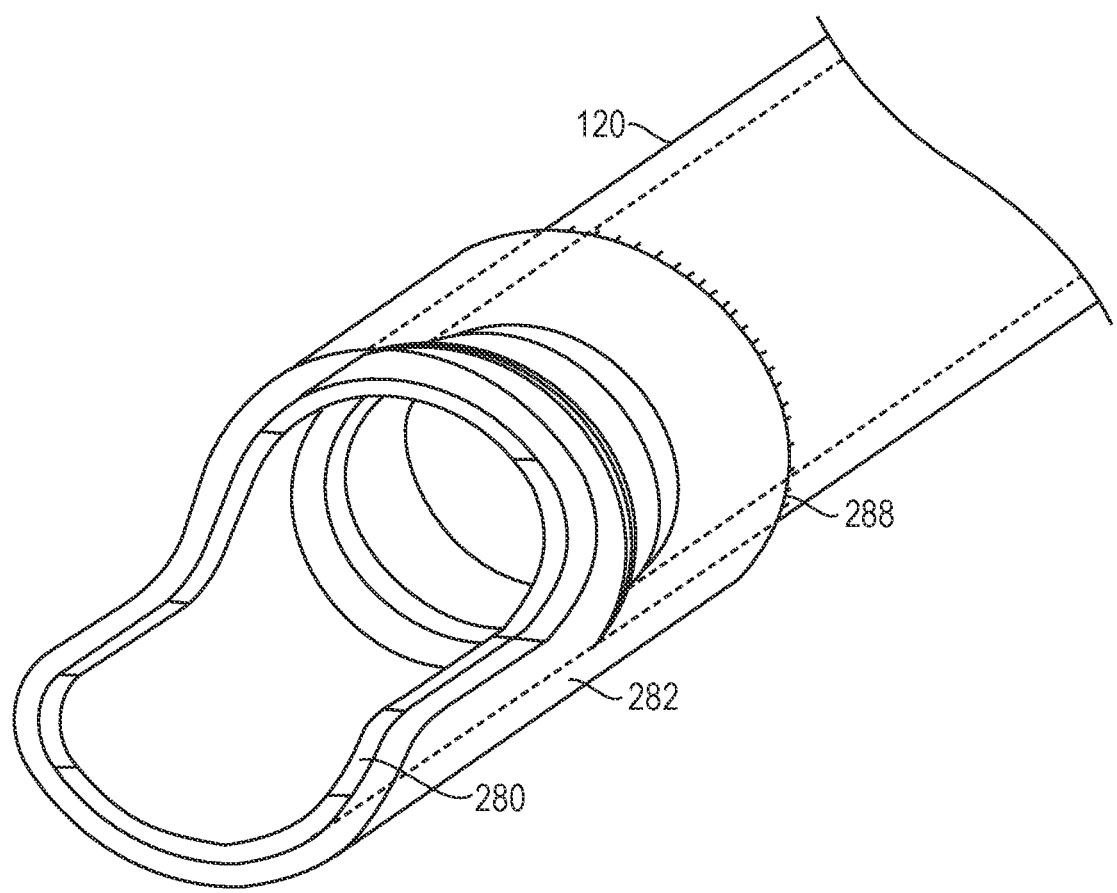
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
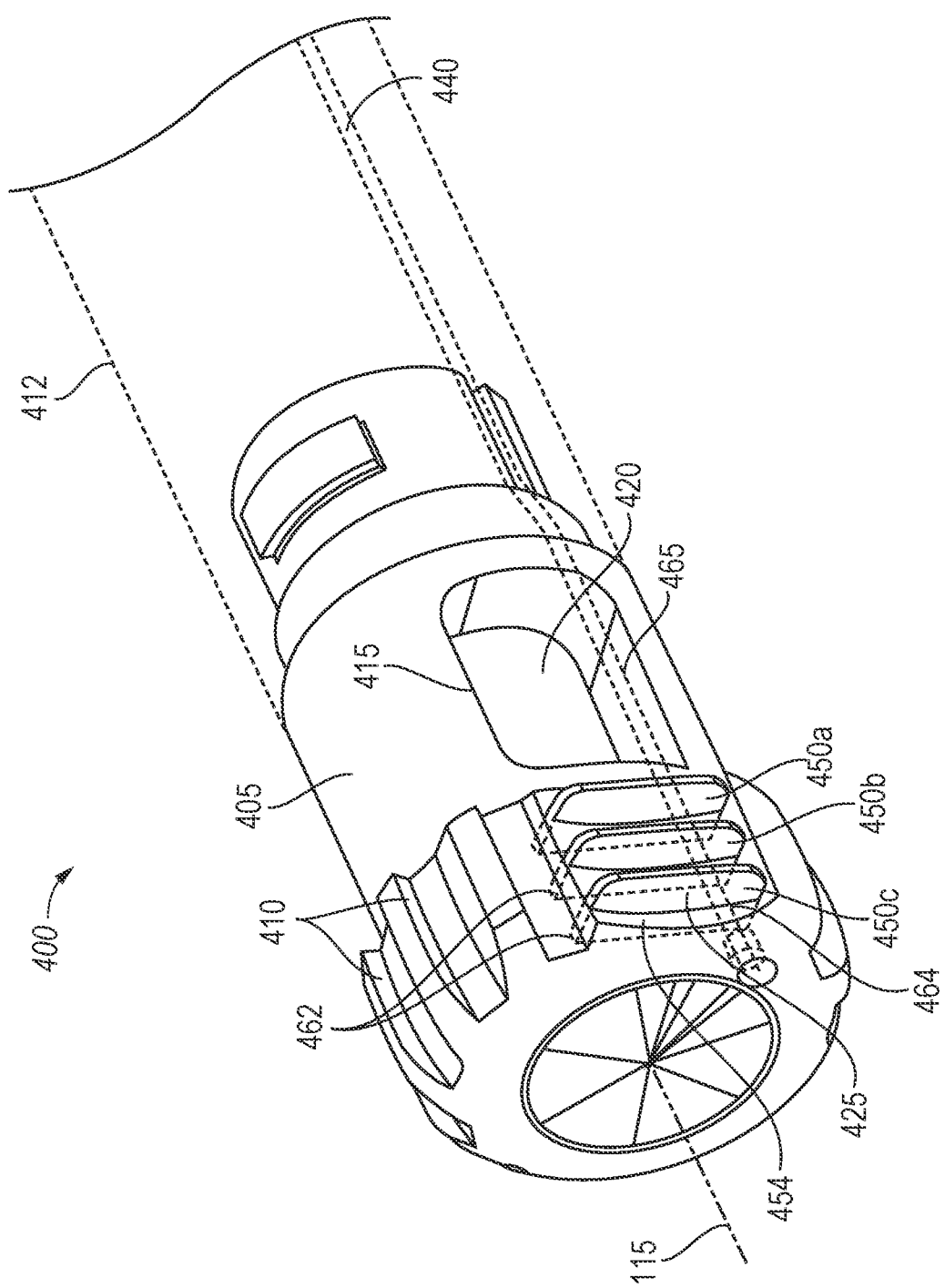
FIG. 9 is a perspective of another variation of a ceramic member with cutting edges that includes an aspiration window and an electrode arrangement positioned distal to the window.
Figure 10:
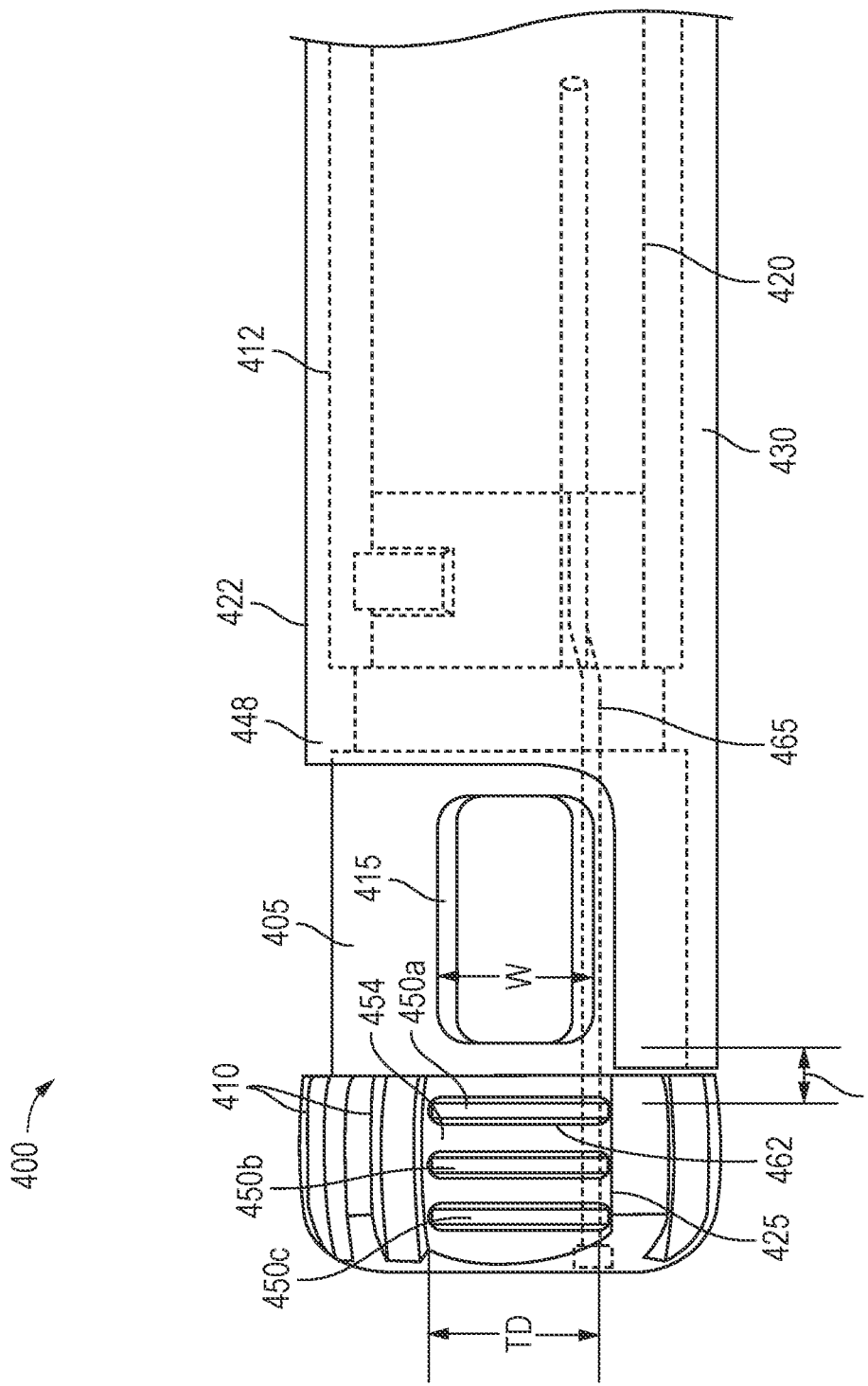
FIG. 10 is an elevational view of a ceramic member and shaft of FIG. 9 showing the width and position of the electrode arrangement in relation to the window.
Figure 11:
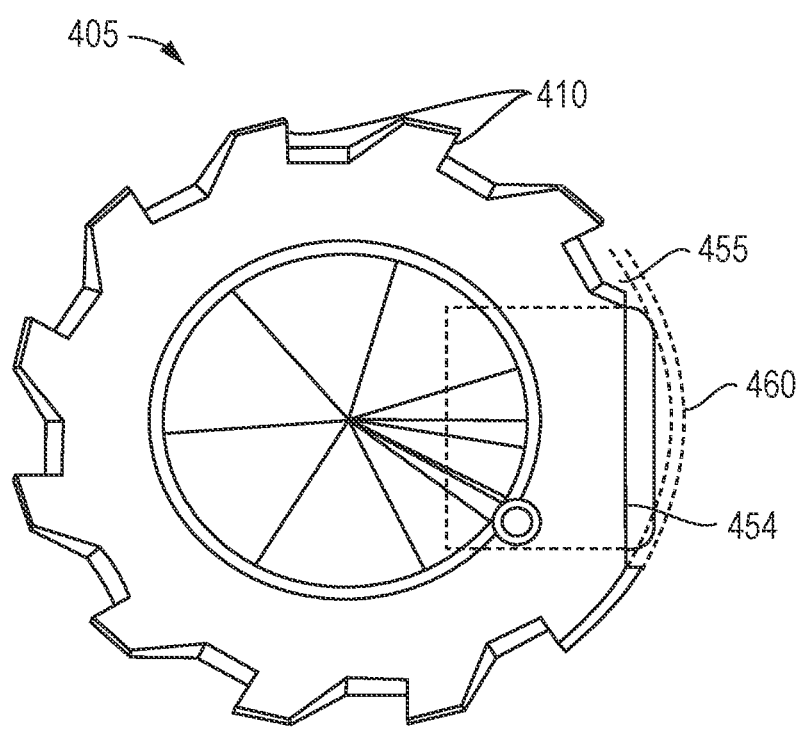
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic member 405 with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulating layer 448, such as Parylene® polymer (a chemical vapor deposited poly(p-xylylene) polymer), to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at 50% of the width of the window, at 80% of the width of the window or at 100% of the width of the window. Further, the system includes a negative pressure source 160 in communication with the interior channel 420.

Figure 12A:
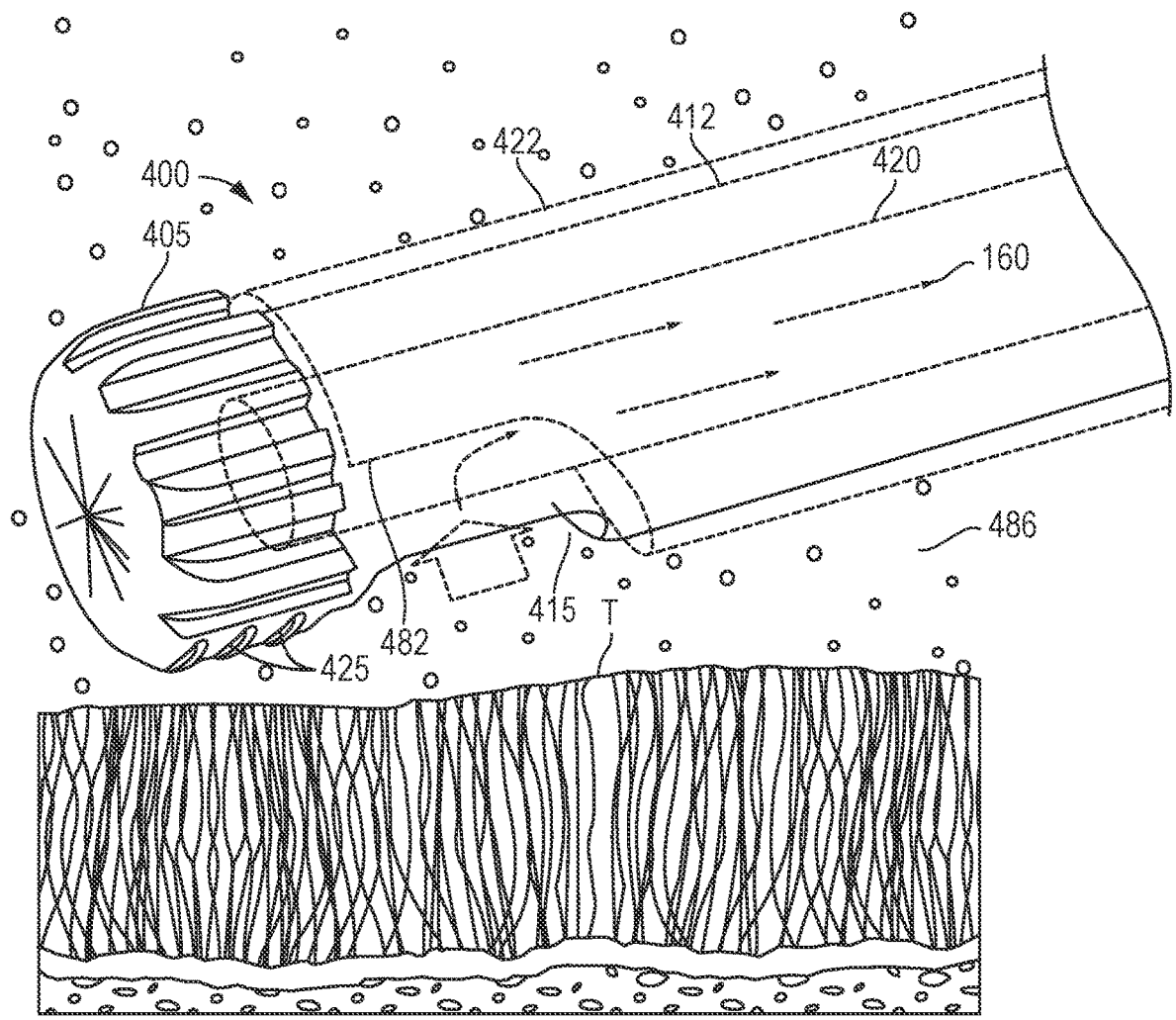
FIG. 12A is a schematic view of the working end and ceramic cutting member of FIGS. 9-11 illustrating a step in a method of use.
Figure 12B:
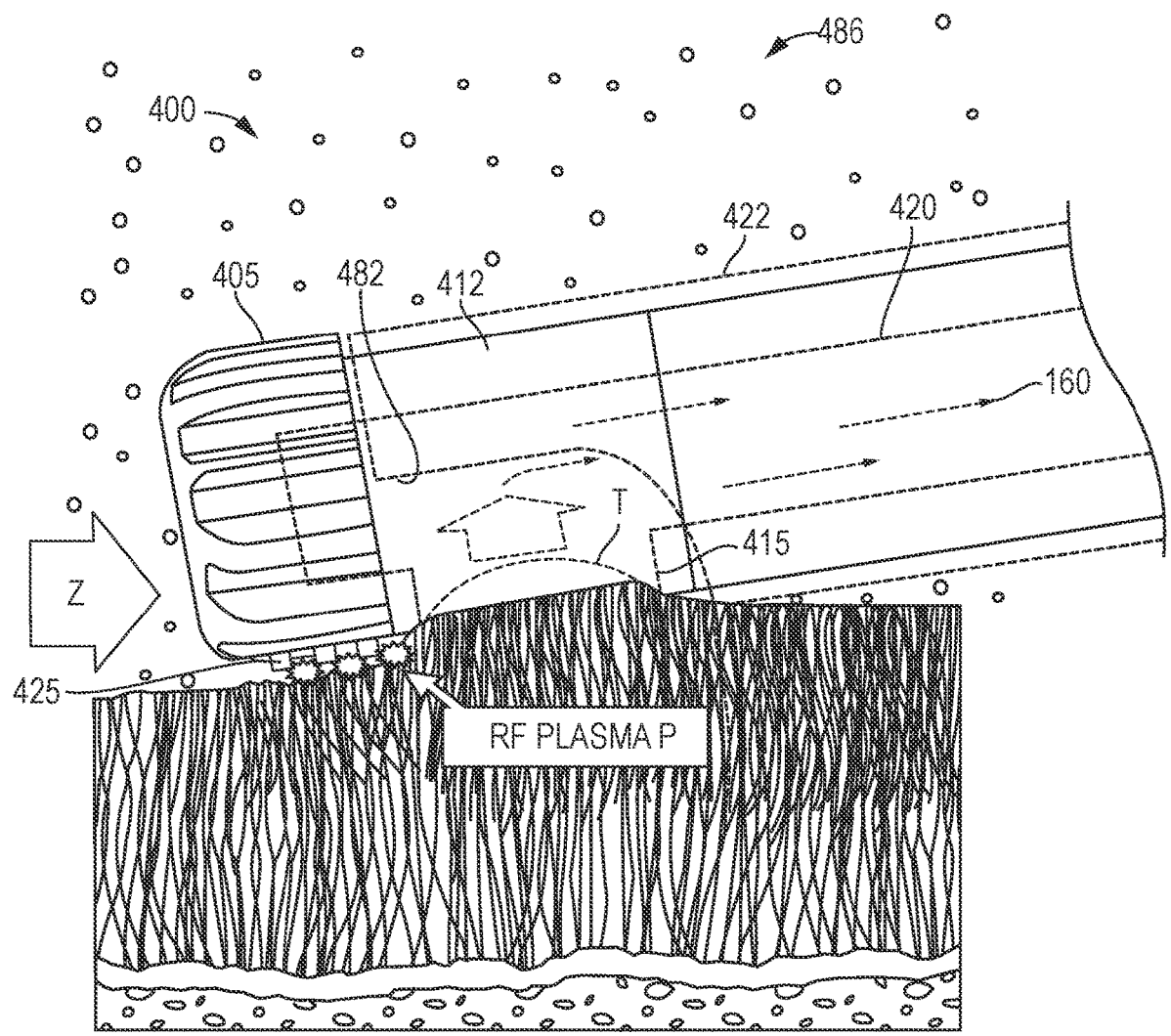
FIG. 12B is another view of the working end of FIG. 12A illustrating a subsequent step in a method of use to ablate a tissue surface.
Figure 12C:
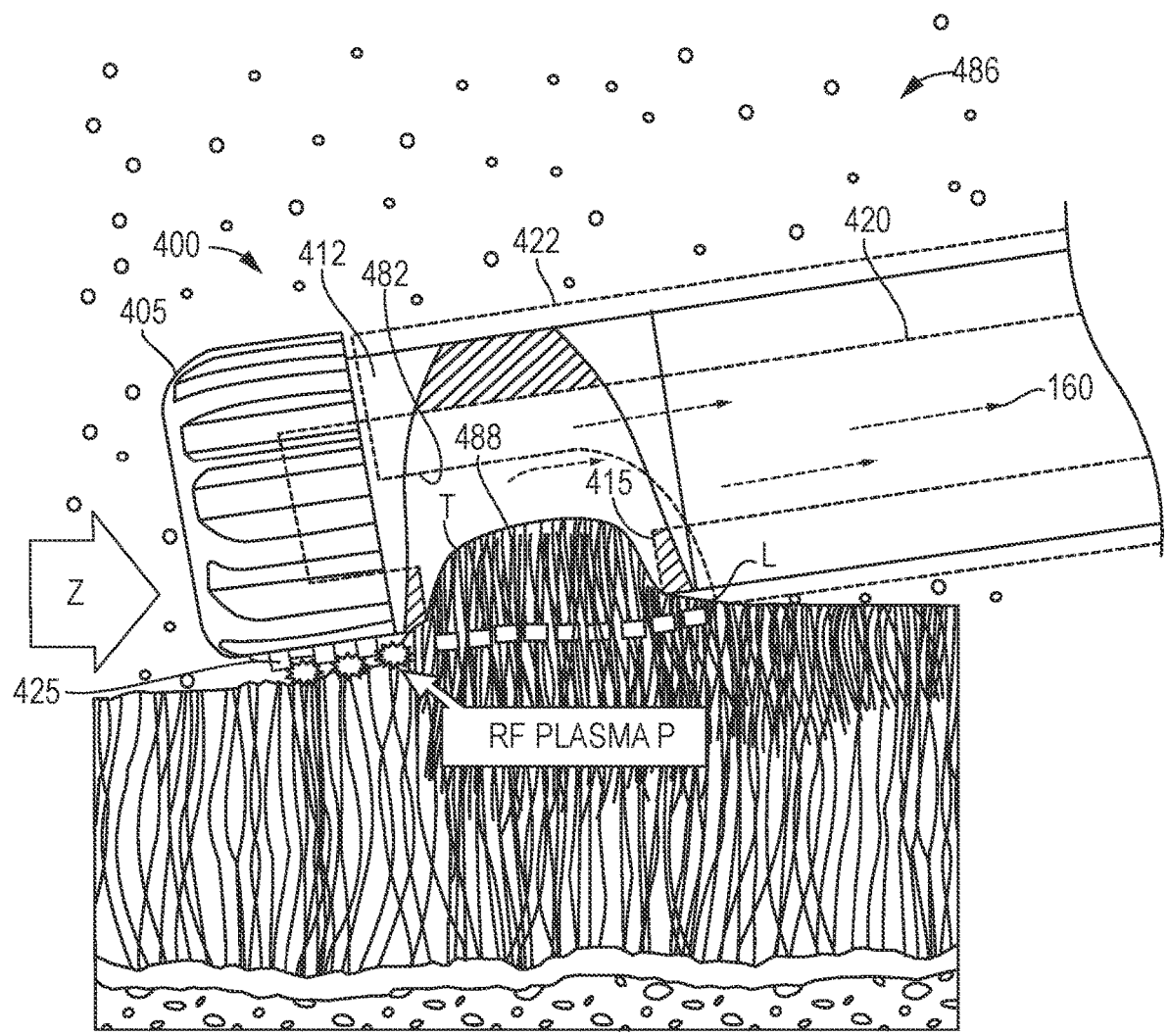
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicated the rotational position of the inner sleeve 412 and ceramic member relative to the outer sleeve 422. The magnet 484b can be positioned in the hub 140B (FIG. 2) so that when sensed by the Hall sensor, the controller algorithm can de-activate the motor drive 105 so as to stop the rotation of the inner sleeve in the selected position.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue greater than 15 grams/min, greater than 20 grams/min, and greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
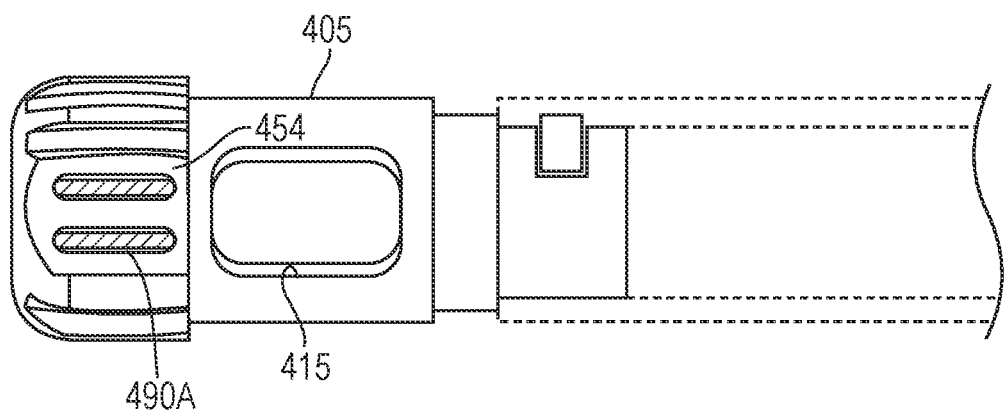
FIG. 13A is an elevational view of an alternative ceramic member and shaft similar to that of FIG. 9 illustrating an electrode variation.
Figure 13B:
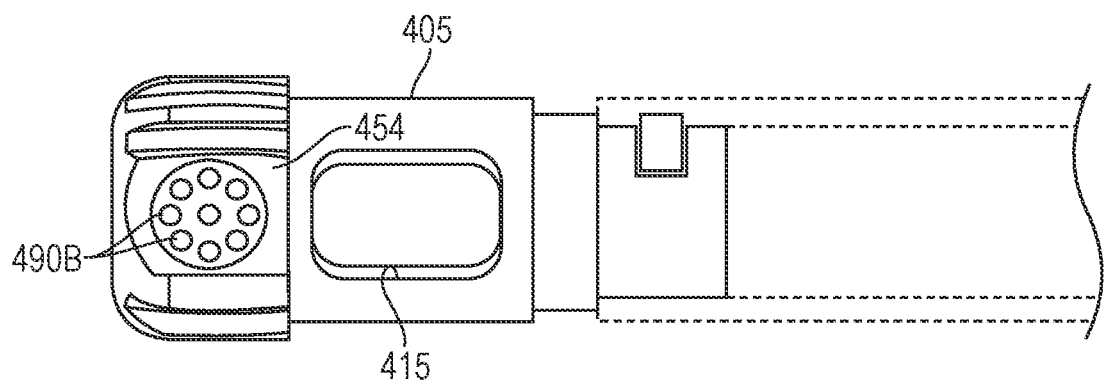
FIG. 13B is an elevational view of another ceramic member similar to that of FIG. 12A illustrating another electrode variation.
Figure 13C:
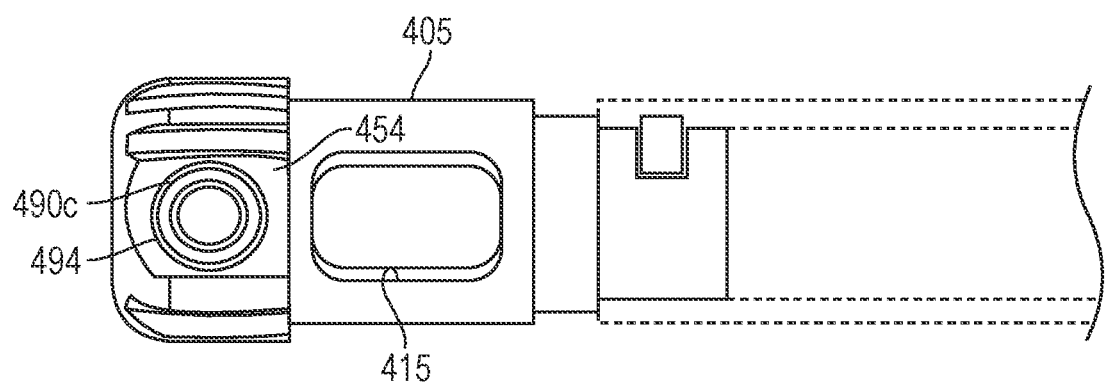
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
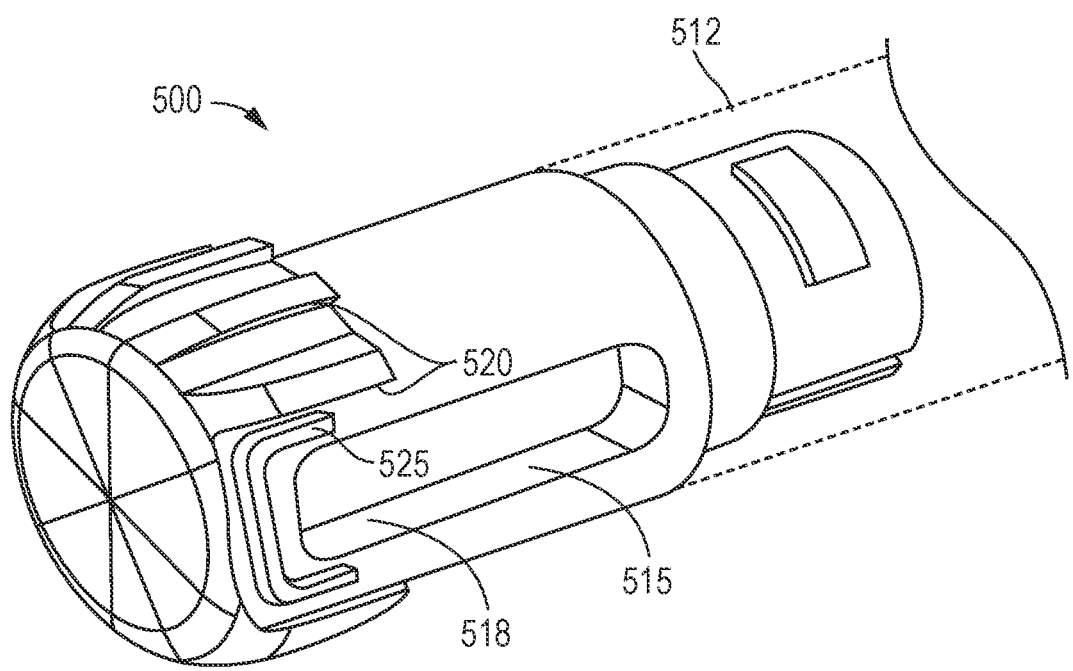
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
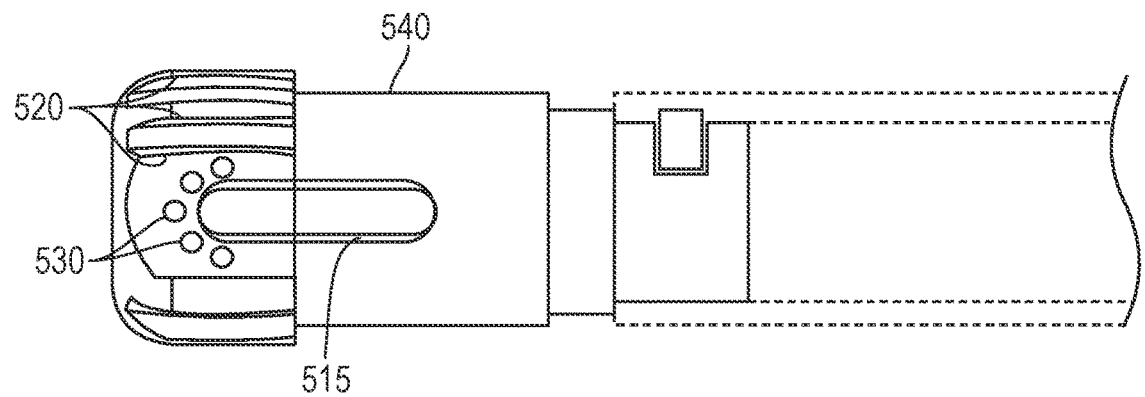
FIG. 15A is an elevational view of a working end variation with an electrode arrangement partly encircling a distal end of the aspiration window.
Figure 15B:
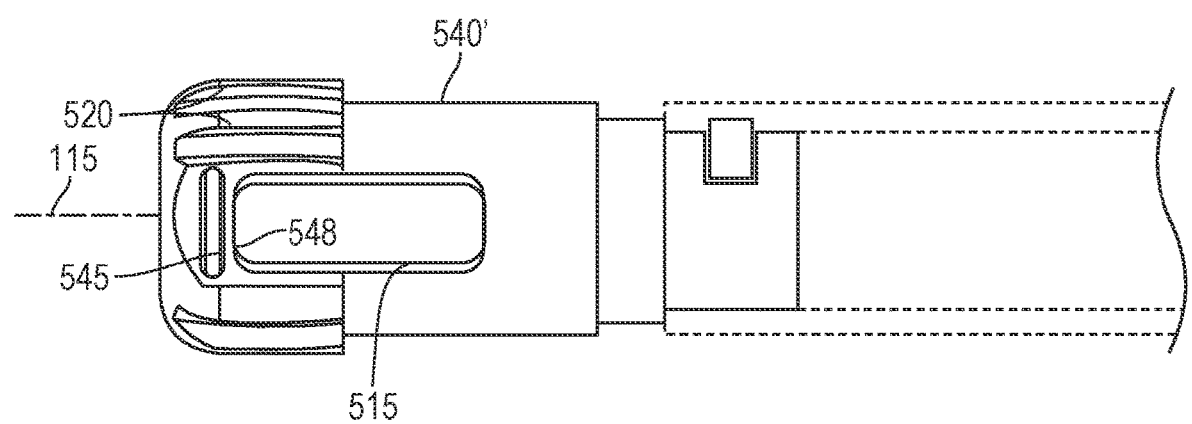
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
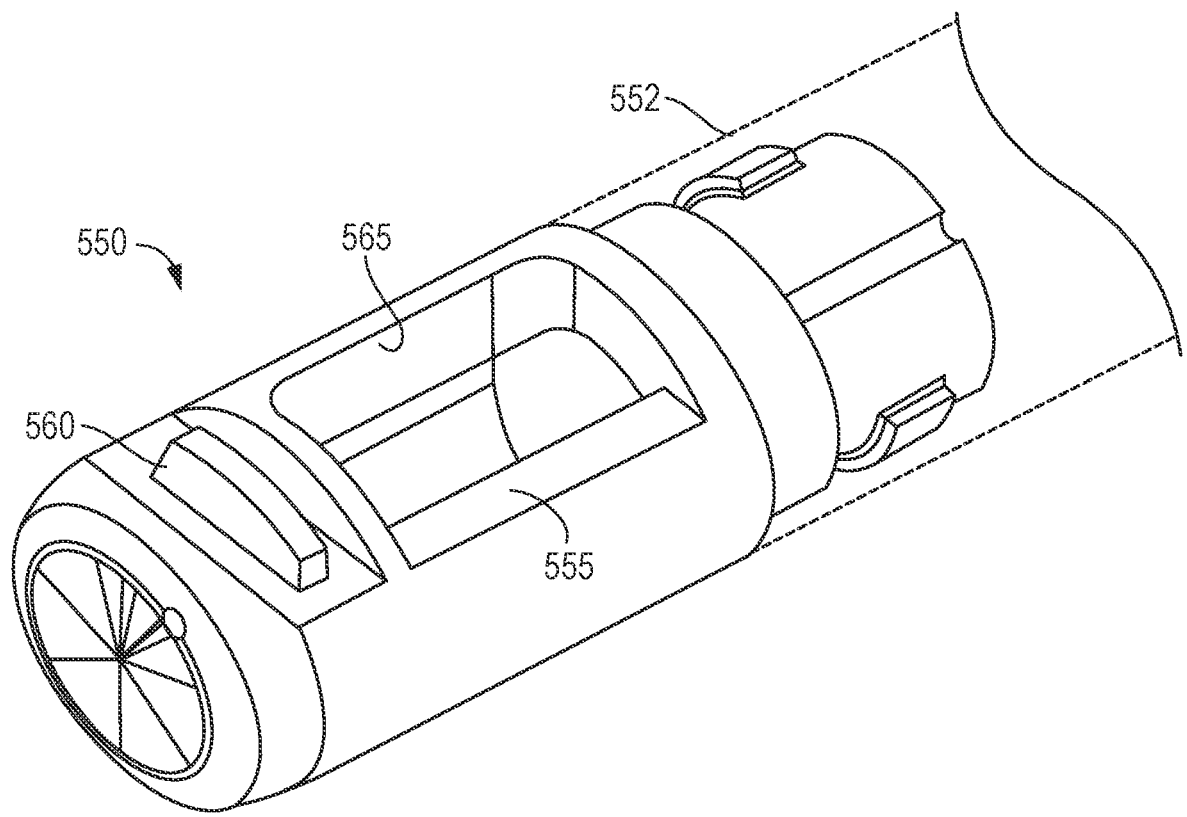
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 rpm. When the ceramic tip member 550 is maintained in a stationary position and translated over targeted tissue, the electrode 560 can be used to ablate surface layers of tissue as described above.

Figure 17:
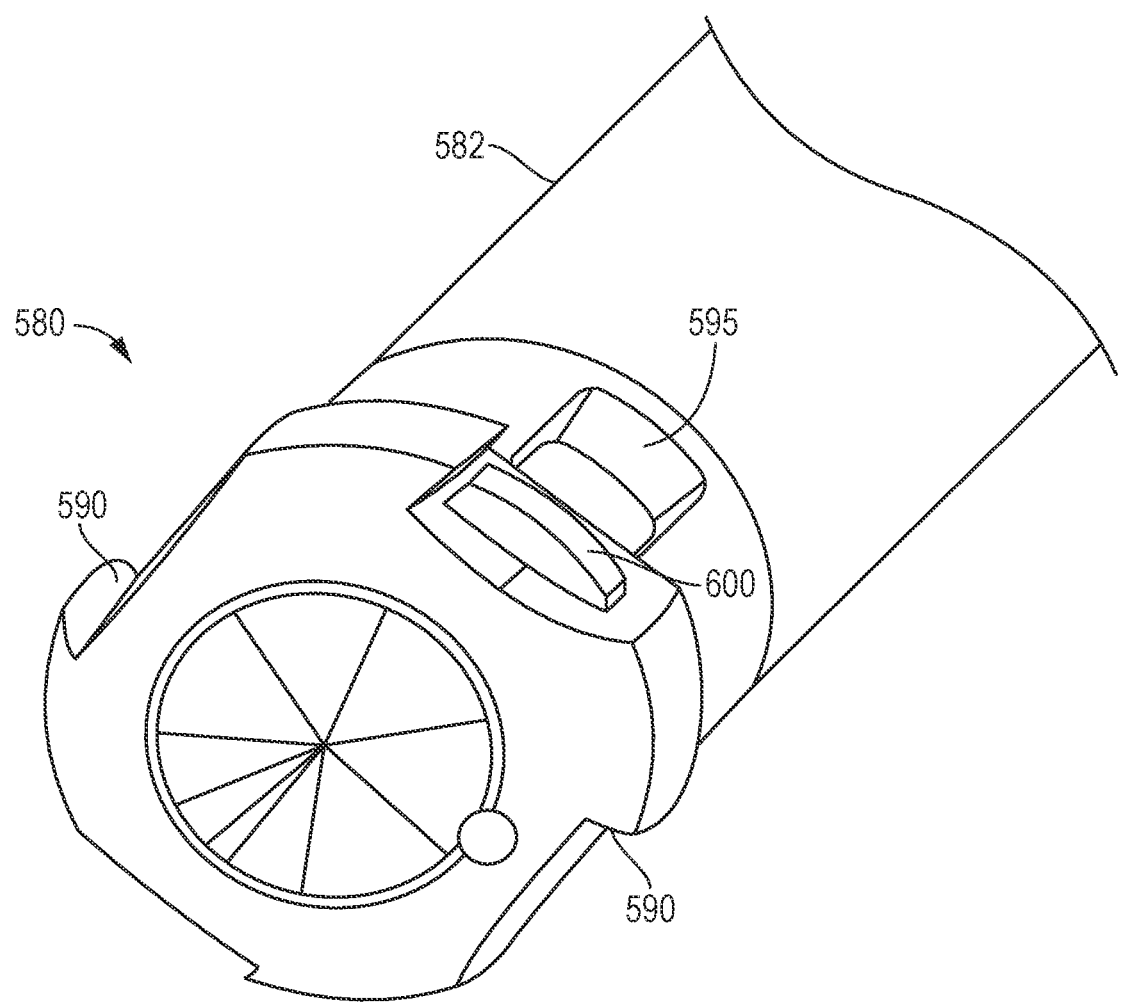
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

Figure 18:
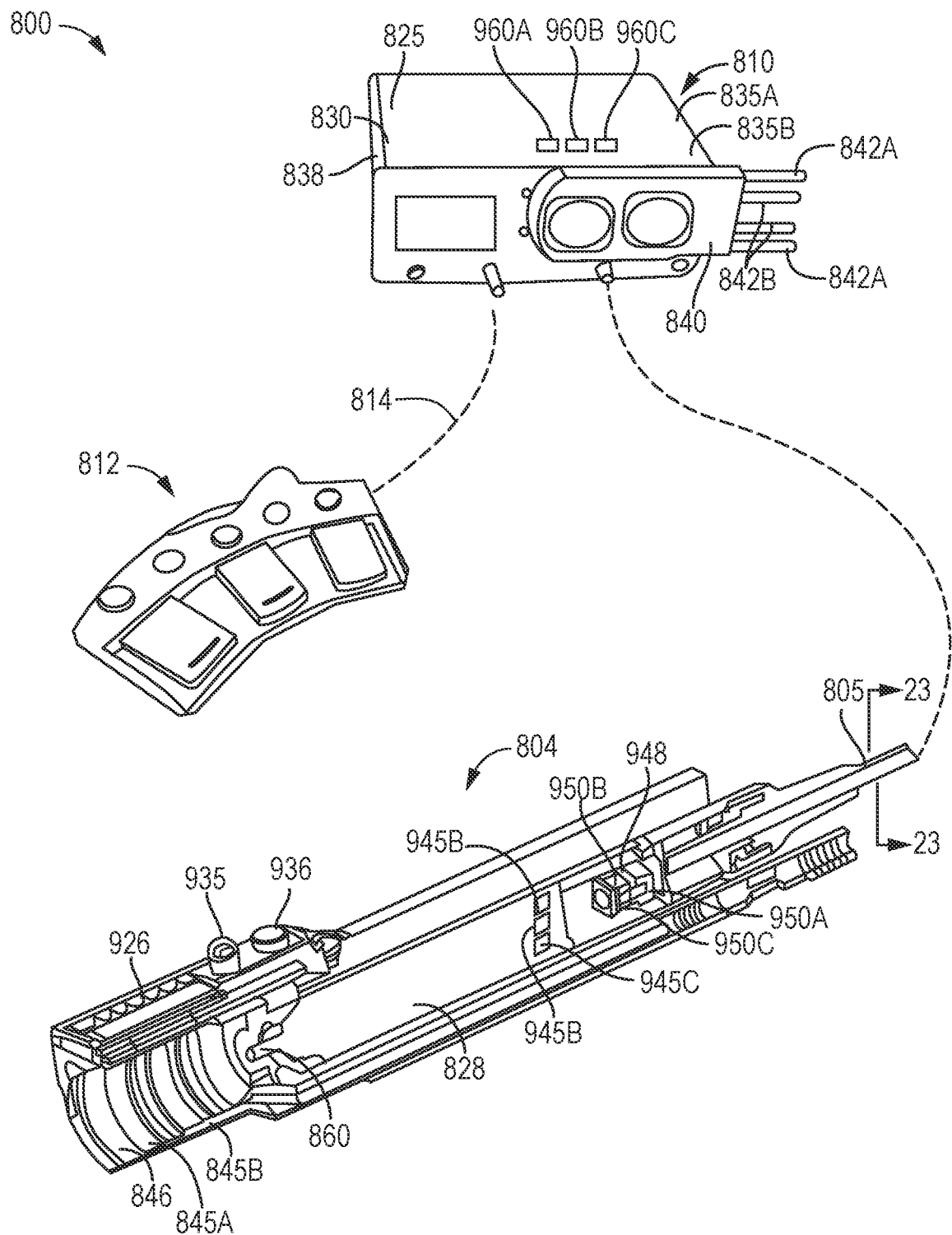
FIG. 18 is perspective view of an arthroscopic system including a control and power console, a footswitch and a re-usable motor carrying a motor drive unit.
Figure 19:
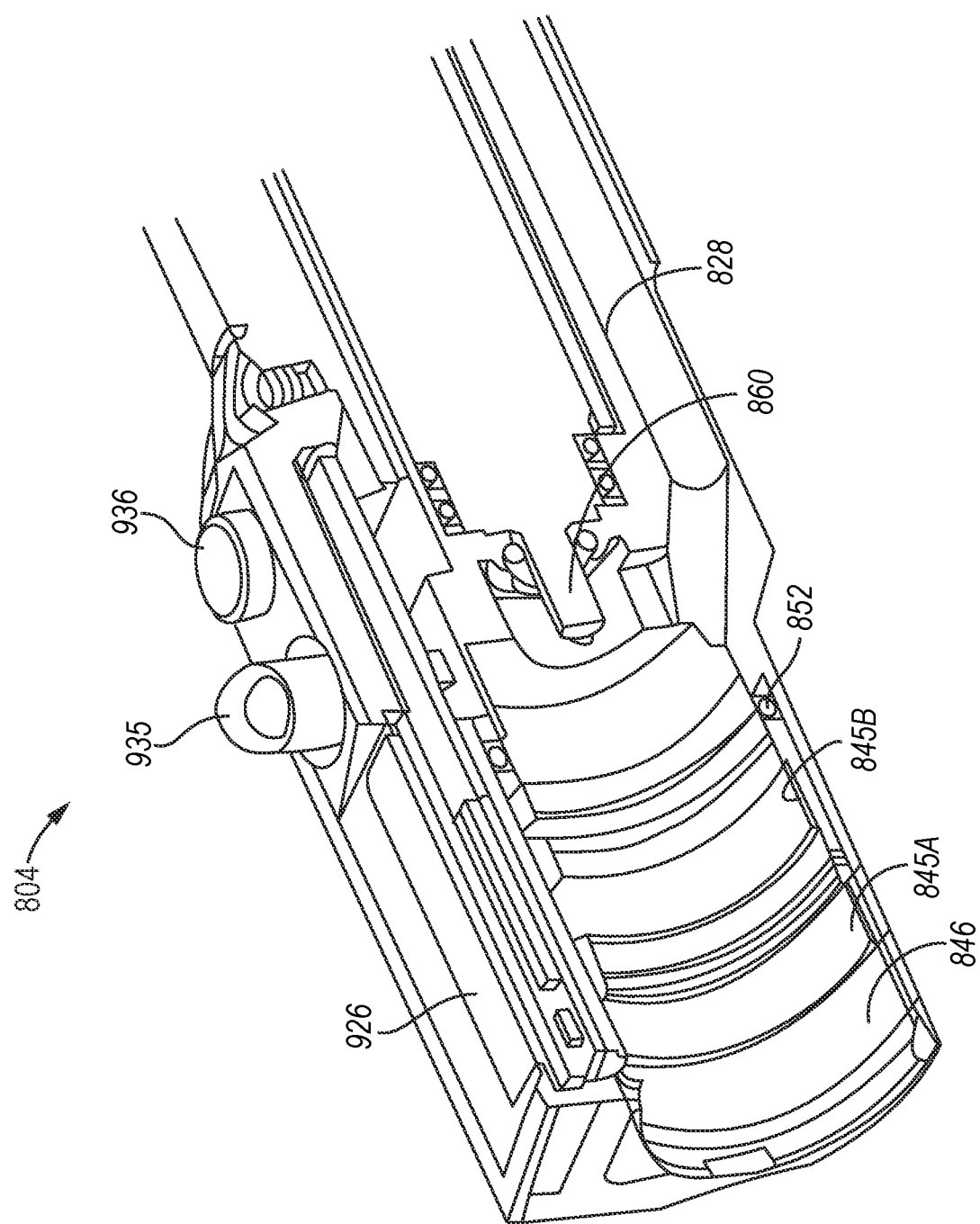
FIG. 19 is an enlarged sectional view of the distal end of the handle of FIG. 18 showing first and second electrical contacts therein for coupling RF energy to a disposable RF probe.
Figure 20:
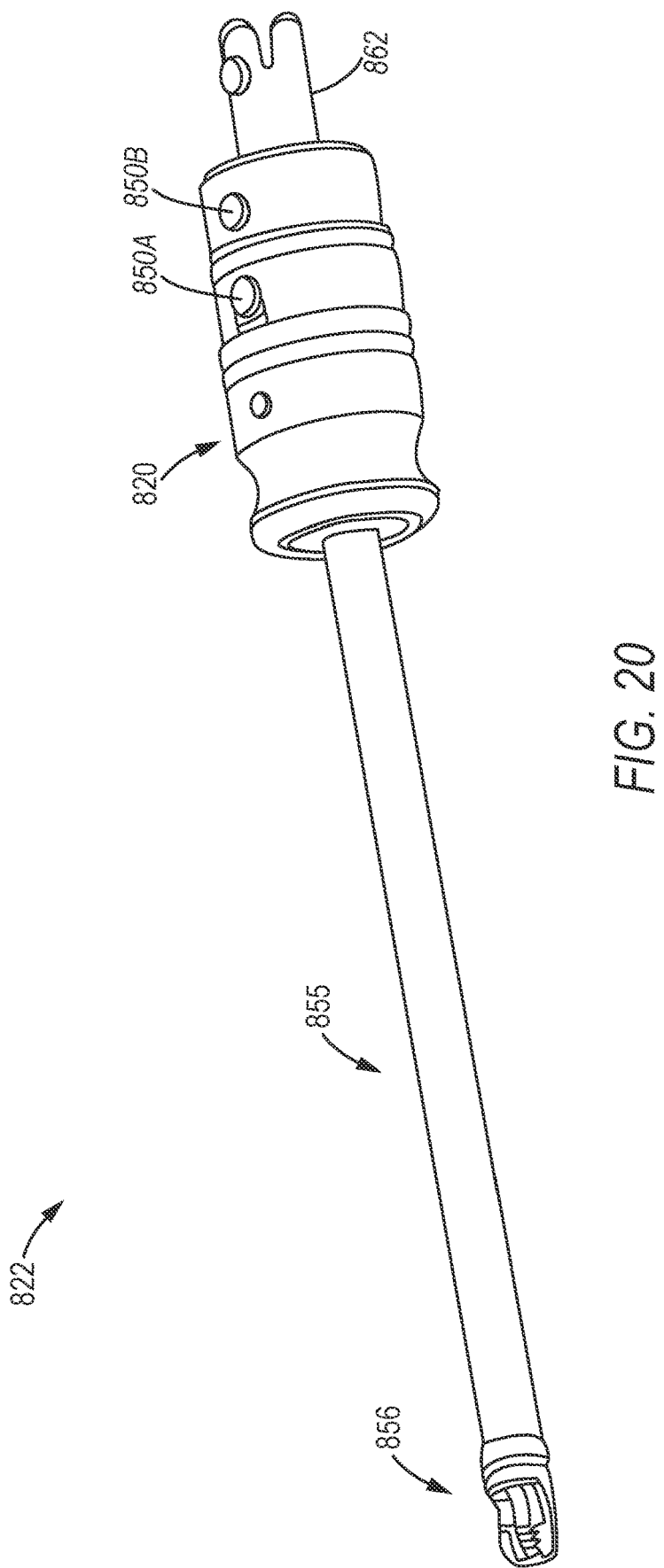
FIG. 20 is a perspective view of a disposable RF probe of the type that couples to the re-useable handle of FIGS. 18-19.

FIGS. 18-21 illustrate components of an arthroscopic system 800 including a re-usable handle 804 that is connected by a single umbilical cable or conduit 805 to a controller unit or console 810. Further, a footswitch 812 is connected by cable 814 to the console 810 for operating the system. As can be seen in FIGS. 18 and 20, the handle 804 is adapted to receive a proximal housing or hub 820 of a disposable shaver or probe 822 with RF functionality of the types shown in FIGS. 9-17 above.

In one variation, the console 810 of FIG. 18 includes an electrical power source 825 for operating the motor drive unit 828 in the handle 804, an RF source 830 for delivering RF energy to the RF electrodes of the disposable shaver 822, and dual peristaltic pumps 835A and 835B for operating the fluid management component of the system. The console 810 further carries a microprocessor or controller 838 with software to operate and integrate all the motor driven and RF functionality of the system. As can be seen in FIG. 18, a disposable cassette 840 carries inflow tubing 842a and outflow tubing 842b that cooperate with inflow and outflow peristaltic pumps in the console 810. The footswitch 812 in one variation includes switches for operating the motor drive unit 828, for operating the RF probe in a cutting mode with radiofrequency energy, and for operating the RF probe in a coagulation mode.

Figure 21:
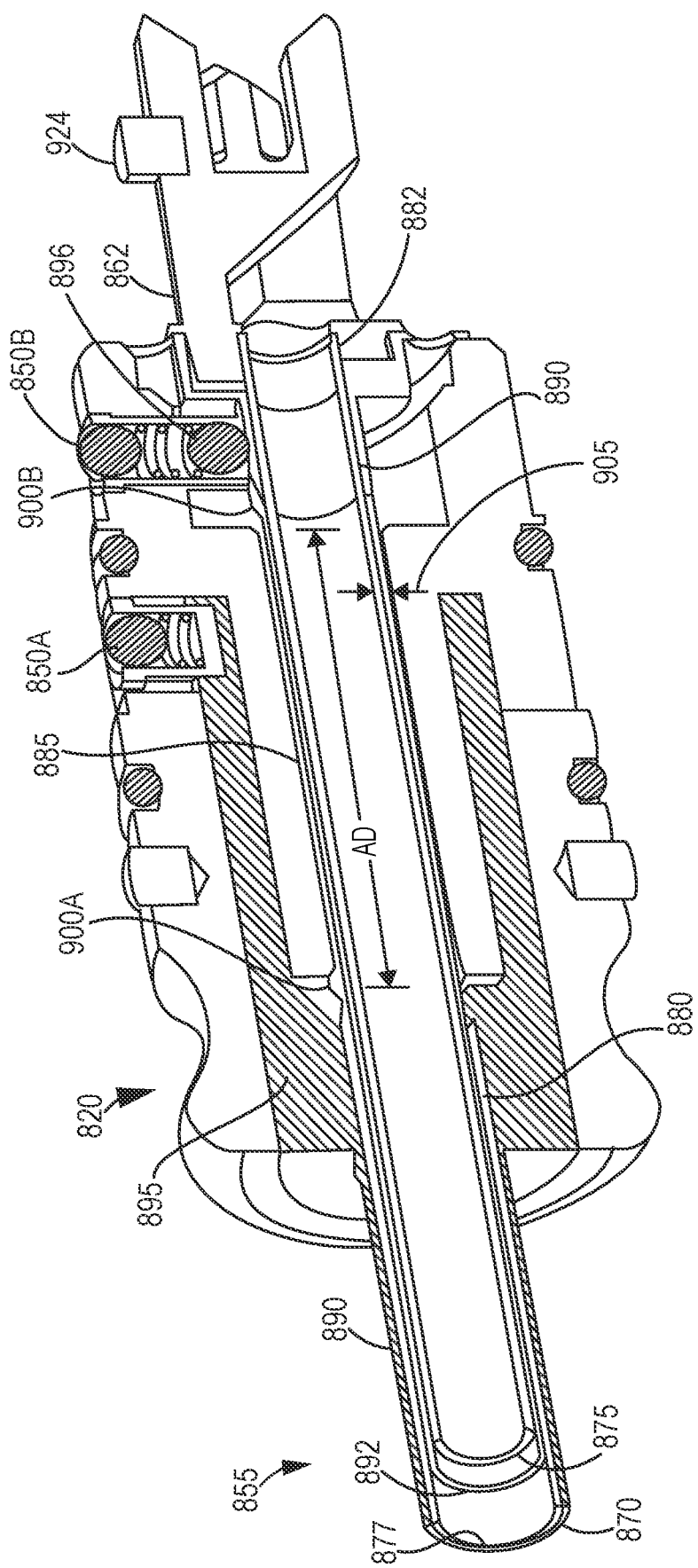
FIG. 21 is a sectional perspective view of a proximal hub portion of the disposable RF probe of FIG. 20.

Of particular interest, the system of the invention includes a handle 804 with first and second electrical contacts 845A and 845B in a receiving passageway 846 of handle 804 (see FIG. 19) that cooperate with electrical contacts 850A and 850B in the proximal hub 820 of the disposable RF shaver 822 (see FIGS. 20-21). The RF shaver 822 has a shaft portion 855 that extends to working end 856 that carries a bi-polar electrode arrangement, of the type shown in FIGS. 9-17. This handle variation further includes providing all the necessary wiring and circuitry within the single conduit 805 that extends between handle 804 and the console 810. For example, the conduit 805 carries electrical leads for a 3-phase motor drive unit 828 in the handle 804, the electrical leads from the RF source 830 to the handle as well as a number of electrical leads for Hall sensors in the motor drive unit 828 that allow the controller 838 to control the operating parameters of the motor drive 828. In this variation, the handle 804 and the conduit 805 are a single component that can be easily sterilized, which is convenient for operating room personnel and economical for hospitals. As can be understood from FIG. 18, the conduit 805 is not detachable from the handle 804.

In the prior art, commercially available shavers that include an RF component utilize an independent RF electrical cable that couples directly to an exposed part of the prior art shaver hub that is exposed distally from the re-usable handle. In such prior art devices, the coupling of RF does not extend through the re-usable handle.

In order to provide a unitary handle 804 and conduit 805 for coupling to console 810 as shown in FIG. 18, a number of innovations are required for (i) coupling RF energy through the handle to the RF shaver, and (ii) in eliminating electrical interference among sensitive Hall sensor circuitry and the higher power current flows to the motor drive unit 828 and to the RF probe 822.

In one aspect of the invention, referring to FIG. 19, it can be seen that the electrical contacts 845A and 845B are cylindrical or partly cylindrical extending around the surface of the receiving passageway 846 of shaver hub 820 (see FIGS. 20-21). In use, it can be understood that such exposed electrical contacts 845A and 845B will be subject to alternating current corrosion, which is also known as stray current corrosion, which terms will be used interchangeably herein. Typically, stainless steel would be used for such electrical contacts. However, it has been found that stainless steel electrical contacts would have a very short lifetime in this application due to corrosion during use.

In this application, if stainless steel electrical contacts were used, alternating currents that would exit such stainless steel contact surfaces would be considered to consist of a blend of capacitive and resistive current. Such resistance is referred to as the polarization resistance, which is the transformation resistance that converts electron conductance into current conductance while capacitance makes up the electrochemical layer of the stainless steel surface. The capacitive portion of the current does not lead to corrosion, but causes reduction and oxidation of various chemical species on the metal surface. The resistive part of the current is the part that causes corrosion in the same manner as direct current corrosion. The association between the resistive and capacitive current components is known in alternating current corrosion and such resistance currents can leads to very rapid corrosion.

In one aspect of the invention, to prevent such alternating current corrosion, the electrical contacts 845A and 845B (FIG. 19) comprise materials that resist such corrosion. In one variation, the first and second electrical contacts 845A and 845B in handle 804 comprise a conductive material selected from the group of titanium, gold, silver, platinum, carbon, molybdenum, tungsten, zinc, Inconel, graphite, nickel or a combination thereof. The first and second electrical contacts 845A and 845B are spaced apart by at least 0.5 mm, 1.0 mm or 1.5 mm. Such electrical contacts can extend radially at least partly around the cylindrical passageway, or can extend in 360° around the cylindrical passageway 846.

In another variation, the hub 820 includes a fluid seal between the hub 820 and passageway 846, such as o-ring 852 in FIG. 19 carried by the handle 804. In another variation, one or more fluid seals can be carried by the hub 820, such as o-rings 854 and 856 shown in FIG. 21. As can be seen in FIG. 21, one such o-ring 856 cam be positioned between the first and second contacts 845A and 845B in the hub 820 and 850A and 850B in the handle.

In general, the arthroscopic system corresponding to the invention provides a re-useable sterilizable shaver handle 804 within an integrated unitary power conduit 805 that carries electrical power for operating a motor drive unit 828 and a bi-polar RF probe 822, wherein the handle 804 includes first and second electrical contacts 845A and 845B that couple to corresponding electrical contacts 850A and 850B in a disposable RF probe 822.

In another aspect of the invention, the electrical contacts 845A and 845B in the handle are provided in a material that is resistant to alternating current corrosion.

In another aspect of the invention, the handle carries a motor drive unit with a rotating shaft 860 that engages a rotating coupler 862 in the hub 820, wherein the shaft 860 is plated or coated with a material resistant to alternating current corrosion.

Referring to FIGS. 20 and 21, another aspect of the invention relates to designs and mechanisms for effectively coupling RF energy from RF source 830 to working end 856 of the RF probe 822 through two thin-wall concentric, conductive sleeves that are assembled into the shaft 855 of the RF probe (see FIG. 21).

FIG. 21 is an enlarged sectional view of the hub 820 of RF probe 822 which illustrates the components and electrical pathways that enable RF delivery to the probe working end 856. More in particular, the shaft 855 comprises an outer sleeve 870 and a concentric inner sleeve 875 that is rotationally disposed in the bore 877 of the outer sleeve 870. Each of the outer sleeve 870 and inner sleeve 875 comprise a thin-wall conductive metal sleeve which carry RF current to and from spaced apart opposing polarity electrodes in the working end 856. In the variation shown in FIG. 21, the inner sleeve 875 comprises an electrical lead to the active electrode in a rotatable shaver component as shown, for example in FIG. 17. In FIG. 21, the outer sleeve 870 is stationary and fixed in hub 820 and has a distal end that comprises a return electrode as is known in the art.

As can be seen in FIG. 21, the outer and inner sleeves, 870 and 875, are separated by insulator layers as will be described below. The proximal end 880 of outer sleeve 870 is fixed in hub 820, for example over-molded with hub 820 of a nonconductive, plastic material. In FIG. 21, the proximal end 882 of the inner sleeve 875 is similarly fixed in a molded plastic coupler 862 that is adapted to mate with splines of shaft 860 of motor drive unit 828. Thus, it can be understood that the assembly of inner sleeve 875 and coupler 862 is adapted to rotate within a passageway 885 in the hub 820 and within bore 877 of outer sleeve 870.

The outer sleeve 870 has an exterior insulating layer 890, such as a heat shrink polymer, that extends distally from hub 820 over the shaft 855. The inner sleeve 875 similarly has a heat shrink polymer layer 892 over it outer surface which electrically separates the inner sleeve 875 from the outer sleeve 870 throughout the length of the shaft 855.

Now turning to the electrical pathways from the handle 804 to the outer and inner sleeves, 870 and 875, it can be seen that a first spring-loaded electrical contact 850A is provided in an exterior surface of hub 820 which is adapted to engage a corresponding electrical contact 845A in the handle 804 as shown in FIG. 19. The electrical contact 850A is connected to a conductive core component 895 within the hub 820 that in turn is coupled to the proximal end 880 of the outer sleeve 870.

FIG. 21 further shows a second spring-loaded electrical contact 850B in hub 820 that is adapted to deliver RF current to the rotating inner sleeve 875. In FIG. 21, the electrical contact 850B has a spring-loaded interior portion 896 that engages collar 890 which in turn is coupled to inner sleeve 875 and coupler 862.

Referring still to FIG. 21, can be seen that the hub assembly 820 and the outer sleeve 870 define a first proximal-most electrical region, herein called a first polarity region 900A, that is exposed to passageway 885 and obviously is electrically un-insulated from said passageway 885. Similarly, the assembly of inner sleeve 875 and collar 890 define a second polarity region 900B that is exposed to passageway 885 extending through hub 820.

It should be appreciated that the RF probe 822 is adapted for use with the working end 856 immersed a conductive saline solution. During use, it will be inevitable that saline will migrate, in part by capillary action, in the proximal direction passageway 885m that is in the annular space comprising the bore 877 of outer sleeve 870 and outward of inner sleeve 875 and its insulator layer 892. Although this annular space or passageway 885 is very small, saline solution still will migrate over the duration of an arthroscopic procedure, which can be from 5 minutes to an hour or more. As can be understood from FIG. 21, the saline eventually will migrate in passageway 885 in the hub 820 and thereafter form an electrically conductive path between the first and second opposing polarity regions 900A and 900B as shown in FIG. 21. If such a conductive saline path between such opposing polarity regions 900A and 900B is formed, it would comprise a short circuit and disrupt RF current flow to and from the working end 856. If such RF current flow through the short-circuit between regions 900A and 900B was insignificant, it could still cause unwanted heating in interior of hub 820. Thus, means are required to prevent or choke any potential RF current flow between the first and second opposing polarity regions 900A and 900B through passageway 885 in hub 820.

In one variation shown in FIG. 21, the longitudinal or axial dimension AD between the first and second opposing polarity regions 900A and 900B is selected to be large enough to substantially or entirely prevent electrical current flow between such regions 900A and 900B due to the high electrical resistance of such a potential current path. In a variation, the axial dimension is at least 0.5", at least 0.6", at least 0.8" or at least 1.0". In such a variation, it is also important to limit the radial dimension of the annular space or gap 905 between the inner and outer sleeves 870 and 875, which can further increases resistance to current flow between the first and second opposing polarity regions 900A and 900B. In a variation, the annular gap 905 has a radial dimension of less than 0.006", less than 0.004" or less than 0.002".

By providing the selected axial dimension AD and radial dimension of the annular gap 905, the potential electrical pathway in a conductive fluid in passageway 885 and any potential unwanted current flow can be eliminated.

Figure 22:
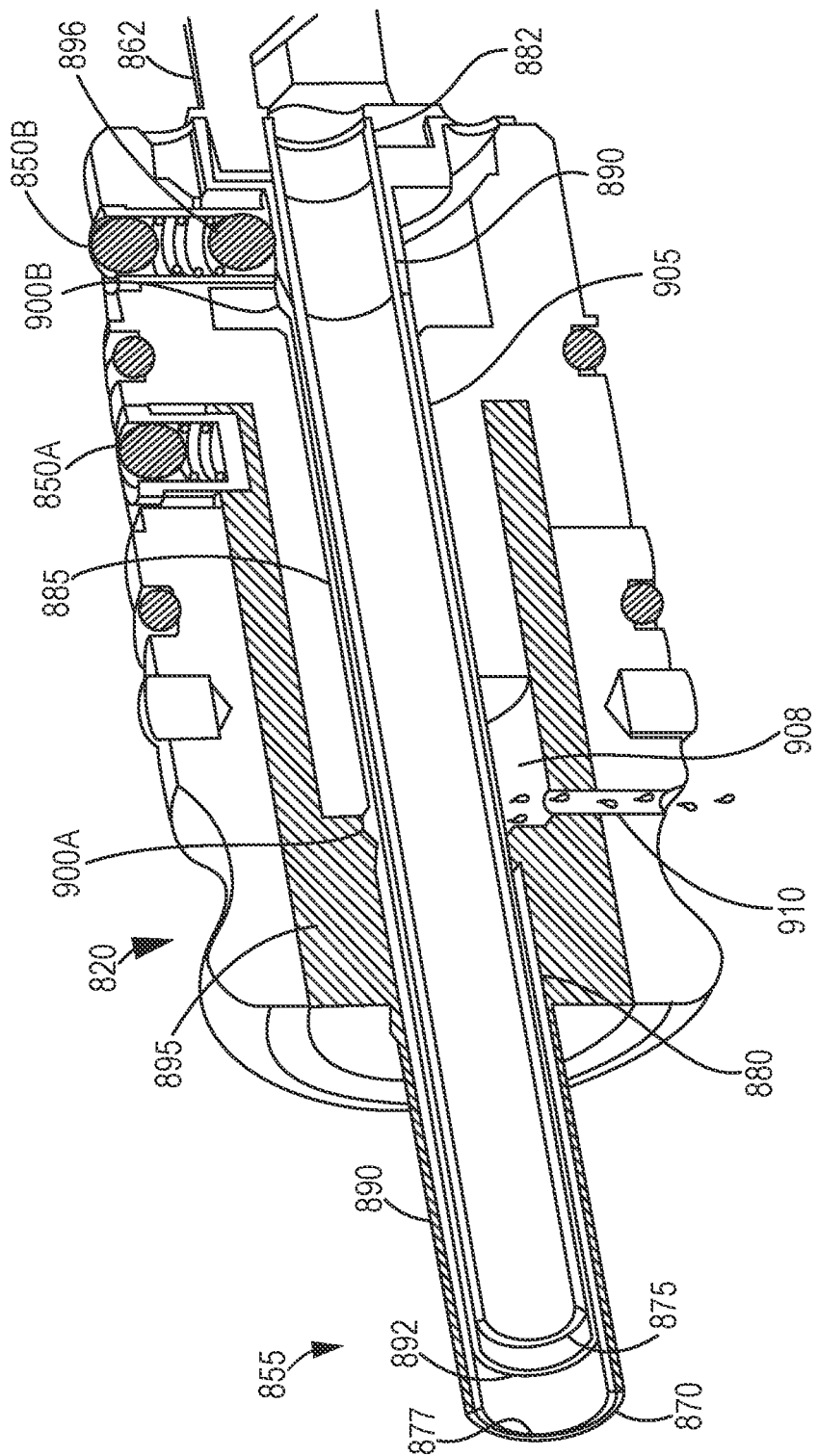
FIG. 22 is a sectional view of a variation of the hub of FIG. 21 which includes a fluid trap for collecting any conductive fluid migrating proximally in the hub.

In other variations, other means can be provided to eliminate conductive saline solution from migrating in the annular gap 905. For example, FIG. 22 show a variation in which an enlarged annular or partly annular space or fluid trap 908 is provided to allow saline to drop by means of gravity into the space 908 and be collected therein. Such a space will prevent capillary action from assisting in the proximal migration of a conductive fluid in passageway 885. In a similar embodiment, still referring to FIG. 22, one or more apertures 910 can be provided in hub 820 to allow any saline in trap 808 to fall outwardly and be removed from the handle 804. In another variation, a desiccant material (not shown) can be exposed to the space 908 to absorb a conductive liquid and thus prevent an electrically conductive pathway between the first and second opposing polarity regions 900A and 900B (see FIG. 22).

FIG. 23 is a sectional view of an alternate handpiece 1200 that includes a fluid outflow channel design that prevents unwanted heating of the handle or handpiece body 1202 by heated fluids passing through the handpiece. It can be understood that the use of RF energy by the working end of an attached RF shaver has the potential to elevate the temperature of irrigation fluid as it passes the electrodes carried by the shaver working end. In this situation, the elevated temperature fluid can increase the temperature of the metal handpiece body 1202.

As can be seen in FIG. 23, the handle body 1202 has a bore 1205 therein that is configured to receive a thin wall outflow sleeve 1210 and is disposed in the bore 1205. More specifically, the outflow sleeve 1210 has a dimension that provides for a surrounding air gap 1220 between the outer wall surface 1222 of sleeve 1210 and the wall of 1225 bore 1205. The air gap 1220 thus provides a significant insulator layer which can prevent heat transfer from any fluid in the outflow sleeve 1210 to the handpiece body 1202.

In general, the arthroscopic device comprises an assembly including a handpiece 1200 coupled to an elongate shaft with a working end carrying at least one electrode for treating tissue and a fluid outflow path in the assembly extending from the working end through a first channel portion in the shaft (see FIGS. 9-12C) that communicates with a second channel portion 1240 in the handpiece body 1202 and wherein second channel portion 1240 includes a thin wall sleeve 1210 substantially surrounded by an air gap 1220 for limiting heat transfer from a fluid outflow to the handpiece body 1202. The sleeve 1210 can comprise a material having a thermal conductivity of less than 50 W/m·K or less than 25 W/m·K. In this variation, the arthroscopic device has an air gap 1220 around an outflow channel or sleeve 1210 that comprises a fluid-tight chamber in the handpiece. The air gap has a transverse dimension of at least 0.005". Further, the device has such a sleeve 1210 that has a sleeve length SL that extends over at least 60% of the length of the second channel portion 1240 in the handpiece, or at least 80% of the length of the second channel portion 1240. The outflow sleeve 1210 can be is at least one of a metal, ceramic or glass, wherein the metal can be a stainless steel. In another variation, the sleeve 1210 can have an exterior or interior surface that comprises a ceramic coating CC which will further prevent heat transfer (see FIG. 23). Alternatively, or in addition to a ceramic coating on sleeve 1210, the bore 1205 in the handpiece body can be lined with ceramic sleeve to reduce heat transfer (not shown).

In a method of the invention, an arthroscopic system is provided which consists of a handpiece coupled to an elongate shaft with an electrosurgical working end, and a negative pressure source for providing a fluid outflow from a treatment site through a flow path in the shaft and handpiece, and the steps of the method comprise: introducing the working end into a fluid-immersed treatment site in a patient's body, activating the electrosurgical working end to treat tissue wherein fluid in the site is heated, activating the negative pressure source to provide an outflow of heated fluid through the outflow path, and limiting heat transfer from the heated fluid to the handpiece with insulation means around the outflow path to thereby maintain the handpiece body at a temperature suitable for gripping with a human hand. In this method, the steps include providing the outflow path through the handpiece within a sleeve member that is substantially surrounded by an air gap 1220.

A number of embodiments of the present invention have been described above in detail, and it should be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A medical device, comprising:
a probe with a proximal hub and an elongate shaft assembly that extends along a first longitudinal axis to a working end of the probe, the working end including at least one electrode for treating tissue, the elongate shaft assembly including an inner sleeve rotatably received in an outer sleeve, the outer sleeve including a proximal end that is fixedly coupled to an outer portion of the proximal hub, the probe including a rotating drive coupling that is fixedly coupled to a proximal end of the inner sleeve, the rotating drive coupling rotatable to rotate the inner sleeve about the first longitudinal axis relative to the outer sleeve and relative to the outer portion of the proximal hub to which the proximal end of the outer sleeve is fixedly coupled, the inner sleeve including a longitudinal channel therein that extends along the first longitudinal axis and provides a fluid outflow path extending proximally from the working end of the probe; and
a handpiece coupled to the proximal hub of the probe, the handpiece including a motor drive configured to couple to the rotating drive coupling for rotating the inner sleeve about the first longitudinal axis relative to the outer sleeve and relative to the outer portion of the proximal hub to which the proximal end of the outer sleeve is fixedly coupled when the proximal hub is coupled to the handpiece, said handpiece comprising a body with a longitudinal bore therein that extends along a second longitudinal axis in the handpiece, the second longitudinal axis being non-coaxial with the first longitudinal axis when the proximal hub is coupled to the handpiece, the handpiece further including a thin-wall sleeve that is received in the longitudinal bore and fixedly secured to the body of the handpiece, the thin-wall sleeve being configured to receive an outflow fluid from the longitudinal channel in the inner sleeve, wherein the thin-wall sleeve is surrounded by an air gap located between an exterior surface of the thin-wall sleeve and an inner surface of the longitudinal bore for limiting heat transfer from the outflow fluid received from the longitudinal channel in the inner sleeve to an exterior of the handpiece, wherein the air gap is provided by a fluid-tight chamber in the handpiece.

2. The medical device of claim 1, wherein the thin-wall sleeve comprises a material having a thermal conductivity of less than 50 W/m·K.

3. The medical device of claim 1, wherein the thin-wall sleeve comprises a material having a thermal conductivity of less than 25 W/m·K.

4. The medical device of claim 1, wherein the thin-wall sleeve has a circumference that extends circumferentially around the second longitudinal axis, and wherein the air gap extends fully around the circumference of the thin-wall sleeve.

5. The medical device of claim 1, wherein the air gap has a width transverse to the second longitudinal axis of at least 0.005".

6. The medical device of claim 1, wherein the thin-wall sleeve extends over at least 60% of a length of the longitudinal bore in the body of the handpiece.

7. The medical device of claim 1, wherein the thin-wall sleeve extends over at least 80% of a length of the longitudinal bore in the body of the handpiece.

8. The medical device of claim 1, wherein the thin-wall sleeve comprises a ceramic material.

9. The medical device of claim 1, wherein the thin-wall sleeve comprises a ceramic coating.

10. A medical device, comprising:
a probe with a proximal hub and an elongate shaft assembly extending distally from the proximal hub to a working end of the probe, the working end including at least one electrode for treating tissue, the elongate shaft assembly including an inner sleeve rotatably received in an outer sleeve, the probe further including a rotating drive coupling that is fixedly coupled to a proximal end of the inner sleeve, the rotating drive coupling rotatable to rotate the inner sleeve within the outer sleeve, the inner sleeve including a longitudinal channel therein that provides a fluid outflow path extending proximally from the working end of the probe; and
a handpiece coupled to the proximal hub of the probe, the handpiece including a motor drive configured to couple to the rotating drive coupling inside the handpiece for rotating the proximal end of the inner sleeve about a first longitudinal axis in the handpiece when the proximal hub is coupled to the handpiece, the handpiece comprising a body with a longitudinal bore therein that extends along a second longitudinal axis in the handpiece, the second longitudinal axis being non-coaxial with the first longitudinal axis in the handpiece, the handpiece further including a thin-wall sleeve that is received in the longitudinal bore in the body of the handpiece, wherein the thin-wall sleeve is configured to receive an outflow fluid from the longitudinal channel in the inner sleeve, the thin-wall sleeve being surrounded by an air gap located between an exterior surface of the thin-wall sleeve and an inner surface of the longitudinal bore for limiting heat transfer from the outflow fluid received from the longitudinal channel in the inner sleeve to an exterior of the handpiece, wherein the air gap is provided by a fluid-tight chamber in the handpiece.

11. The medical device of claim 10, wherein the thin-wall sleeve and a surrounding portion of the body of the handpiece have a combined thermal conductivity in a transverse direction of less than 25 W/m·K.

12. The medical device of claim 10, wherein the thin-wall sleeve is formed at least partly of a material selected from a group consisting of metal, ceramic and glass.

13. The medical device of claim 12, wherein the thin-wall sleeve is formed at least partly of stainless steel.

14. The medical device of claim 12, wherein the thin-wall sleeve is formed at least partly of a metal with a ceramic surface layer.

15. The medical device of claim 12, wherein the thin-wall sleeve is formed at least partly of a ceramic providing an exterior or interior surface of the thin-wall sleeve.

16. The medical device of claim 10, wherein the thin-wall sleeve comprises a material having a thermal conductivity of less than 25 W/m·K.

17. The medical device of claim 10, wherein the thin-wall sleeve has a circumference that extends circumferentially around the second longitudinal axis, and wherein the air gap extends fully around the circumference of the thin-wall sleeve.

18. The medical device of claim 10, wherein the air gap has a width transverse to the second longitudinal axis of at least 0.005".

19. The medical device of claim 10, wherein the thin-wall sleeve extends over at least 60% of a length of the longitudinal bore in the body of the handpiece.

20. The medical device of claim 10, wherein the longitudinal bore in the body of the handpiece is positioned laterally of the first longitudinal axis in the handpiece such that the entirety of the first longitudinal axis is located outside the longitudinal bore in the body of the handpiece.

* * * * *